United States Patent
Wang et al.

(10) Patent No.: US 11,827,612 B2
(45) Date of Patent: Nov. 28, 2023

(54) HYDROXAMIC ACID DERIVATIVE, METHOD FOR PRODUCING SAME AND USE THEREOF

(71) Applicant: INSTITUTE OF MEDICINAL BIOTECHNOLOGY, CHINESE ACADEMY OF MEDICAL SCIENCES, Beijing (CN)

(72) Inventors: Yucheng Wang, Beijing (CN); Xuefu You, Beijing (CN); Juxian Wang, Beijing (CN); Xiaonan Du, Beijing (CN); Minghua Wang, Beijing (CN); Mei Zhu, Beijing (CN); Guoning Zhang, Beijing (CN)

(73) Assignee: INSTITUTE OF MEDICINAL BIOTECHNOLOGY, CHINESE ACADEMY OF MEDICAL SCIENCES, Beijing (CN)

( * ) Notice: Subject to any disclaimer, the term of this patent is extended or adjusted under 35 U.S.C. 154(b) by 228 days.

(21) Appl. No.: 17/421,755

(22) PCT Filed: Sep. 16, 2020

(86) PCT No.: PCT/CN2020/115509
§ 371 (c)(1),
(2) Date: Jul. 9, 2021

(87) PCT Pub. No.: WO2021/052353
PCT Pub. Date: Mar. 25, 2021

(65) Prior Publication Data
US 2022/0033369 A1    Feb. 3, 2022

(30) Foreign Application Priority Data
Sep. 19, 2019 (CN) .......................... 201910885618.3

(51) Int. Cl.
| | | |
|---|---|---|
| A61P 31/04 | (2006.01) | |
| C07D 295/155 | (2006.01) | |
| C07D 295/195 | (2006.01) | |
| C07D 295/215 | (2006.01) | |
| C07C 259/06 | (2006.01) | |
| C07C 41/30 | (2006.01) | |
| C07C 51/09 | (2006.01) | |
| C07C 67/343 | (2006.01) | |
| C07C 231/12 | (2006.01) | |
| C07C 269/06 | (2006.01) | |

(52) U.S. Cl.
CPC ........ *C07D 295/195* (2013.01); *C07C 259/06* (2013.01); *C07D 295/155* (2013.01)

(58) Field of Classification Search
CPC . A61P 31/04; C07D 295/155; C07D 295/195; C07D 295/215; C07B 2200/07; C07C 259/06; C07C 2601/08; C07C 41/30; C07C 45/29; C07C 51/09; C07C 67/343; C07C 231/12; C07C 269/06
See application file for complete search history.

(56) References Cited

FOREIGN PATENT DOCUMENTS

| | | |
|---|---|---|
| CN | 1777577 A | 5/2006 |
| CN | 101765585 A | 6/2010 |
| CN | 110563611 A | 12/2019 |
| WO | 2004/062601 A2 | 7/2004 |
| WO | 2008/154642 A2 | 12/2008 |
| WO | 2012/031298 A2 | 3/2012 |
| WO | 2013/039947 A1 | 3/2013 |
| WO | 2017/189586 A1 | 11/2017 |
| WO | 2017/223349 A1 | 12/2017 |
| WO | 2018/115432 A2 | 6/2018 |

OTHER PUBLICATIONS

International Search Report dated Dec. 16, 2020, International Application No. PCT/CN2020/115509, pp. 1-6.
Xiaonan Du et al., "Improved Synthesis of LpxC Inhibitor ACHN-975," Chinese Journal of Pharmaceuticals, vol. 50, No. 5, 2019, pp. 514-519 (Includes English Translation of Abstract).

*Primary Examiner* — Brenda L Coleman

(57) ABSTRACT

The present disclosure is related to the field of enzyme inhibitors, and in particular to a hydroxamic acid derivative, a method for producing the same and use thereof. The hydroxamic acid group of the hydroxamic acid derivative can be chelated with zinc ions in the LpxC active area, and the derivative has a hydrophobic side chain which can bind to hydrophic channels in the enzyme LpxC. These guarantee that the hydroxamic acid derivative has good bactericidal activity against Gram-negative bacteria and low toxicity. The present disclosure also provides a method for producing the hydroxamic acid derivative, which requires a shorter reaction time and can provide the derivative with a high yield.

19 Claims, No Drawings

HYDROXAMIC ACID DERIVATIVE, METHOD FOR PRODUCING SAME AND USE THEREOF

This application claims the benefit of priority of Chinese Application No. 201910885618.3 filed Sep. 19, 2019, entitled "HYDROXAMIC ACID DERIVATIVE, METHOD FOR PRODUCING SAME AND USE THEREOF", the entire disclosure of which is incorporated herein by reference.

TECHNICAL FIELD

The present disclosure is related to the field of enzyme inhibitors, and in particular to a hydroxamic acid derivative, a method for producing the same and use thereof.

BACKGROUND

Super bacteria and human beings have been fighting each other for a very long period of time. Alexander Fleming discovered penicillin in the 1930's, and the first antibiotic was then born. At the same time, however, bacteria began to struggle against antibiotics and evolve. Today, the issue of bacterial resistance to antibiotics is a more and more serious problem. However, development of novel antibiotics is lagging behind. Around 700,000 people worldwide die annually because of infection by resistant bacteria, and around 230,000 newborn infants die annually because of this. If we fail to develop novel antibiotics in time to control the spread of super bacteria, it is predicted that there would be around 10 million people died from bacterial infections in 2050. At that time, super bacteria will become the first leading cause of death in the world.

UDP-3-O—(R-3-hydroxymyristol)-N-acetylglucosamine deacetylase (LpxC) is a key enzyme in catalyzed synthesis of lipid A which is a major component of lipopolysaccharides in the Gram-negative bacterial outer membrane. It is found in the Gram-negative bacteria with high homology, and has no sequence in common with the various enzymes from mammals (including human beings). Deficiency or overexpression of LpxC can cause death of certain Gram-negative bacteria, which makes it a particular interesting target for development of drugs resistant to Gram-negative bacteria.

Over the past more than twenty years, scientists have designed and synthesized various types of LpxC inhibitors. Although many of these compounds have been reported to show excellent preclinical data, it is still desired to provide a novel LpxC inhibitor, which exhibits bactericidal activity against Gram-negative bacteria and has acceptable toxicity or tolerability.

SUMMARY

An objective of the present disclosure is to provide a hydroxamic acid derivative, a method for producing the same and use thereof, the hydroxamic acid derivative exhibiting good bactericidal activity against Gram-negative bacteria and low toxicity.

One objective of the present disclosure is realized by a hydroxamic acid derivative having a structure of following Formula (I):

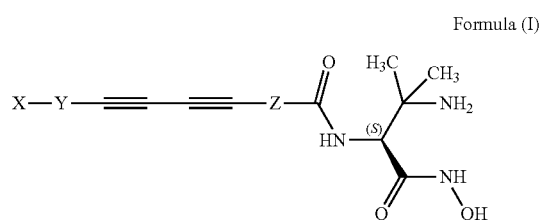

Formula (I)

where,
X is

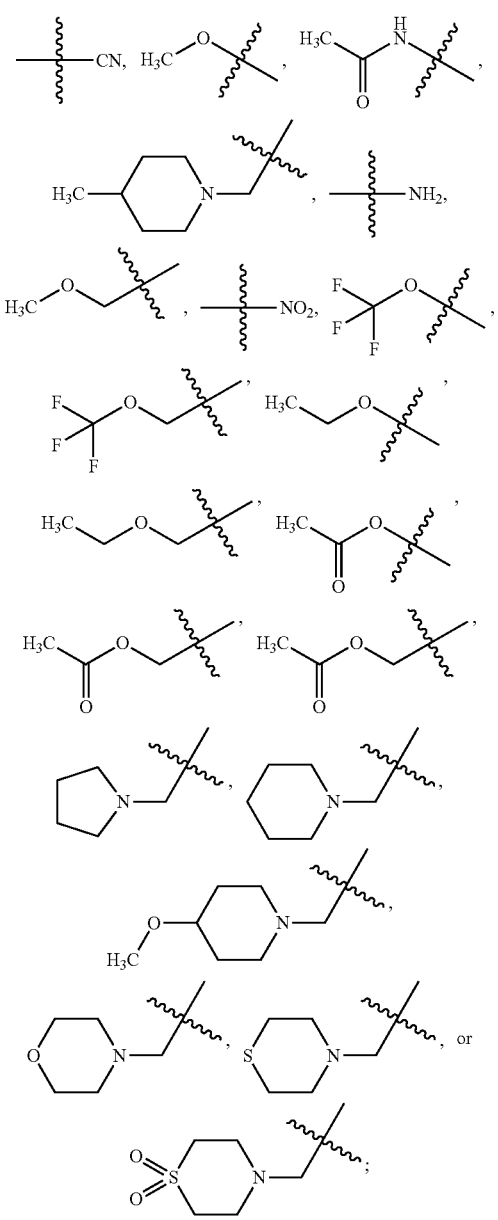

Y is

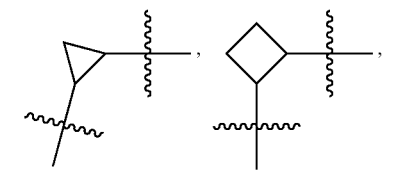

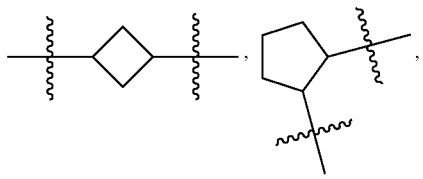

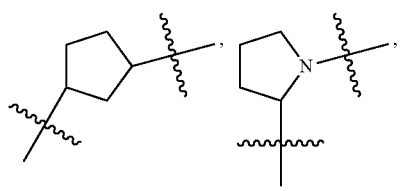

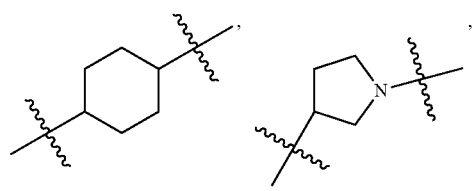

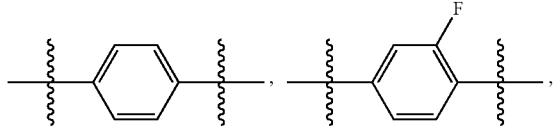

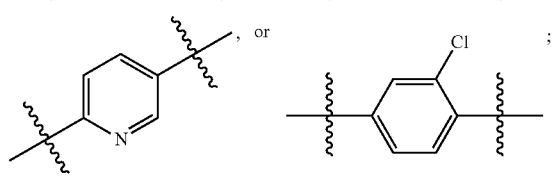

and

Z is

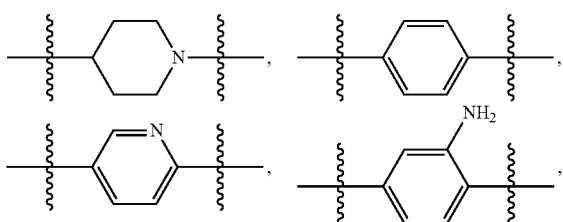

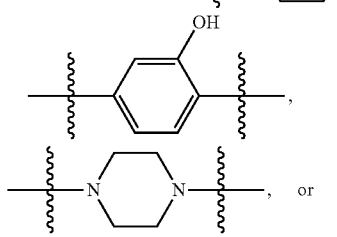

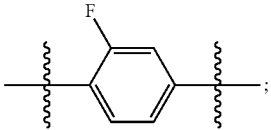

where, when Y and Z are

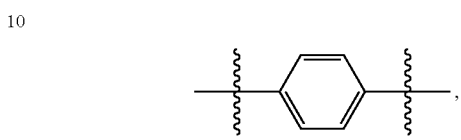

X is not

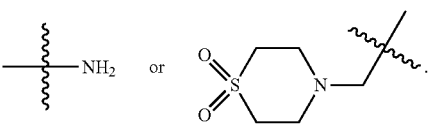

In a preferred embodiment, X is

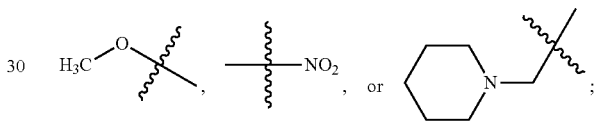

Y is 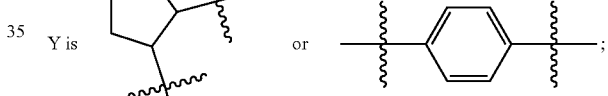

and Z is 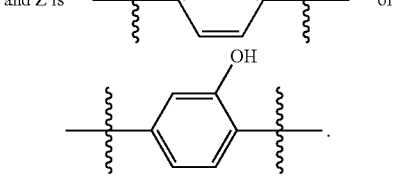

Another aspect of the present disclosure provides a method for producing the hydroxamic acid derivative as described above, including steps of:

mixing a compound having a structure of following Formula (II) with Dess-Martin periodinane and dichloromethane to conduct an oxidation reaction, so as to obtain a compound having a structure of following Formula (III);

  Formula (II)

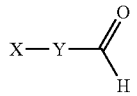  Formula (III)

mixing the compound of Formula (III) with triphenylphosphine, carbon tetrabromide (CBr₄), and dichloromethane to conduct the Corey-Fuchs reaction, so as to obtain a compound having a structure of following (IV);

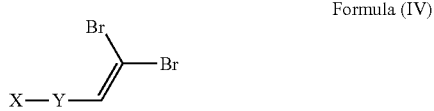

Formula (IV)

mixing the compound of Formula (IV) with tris(dibenzylideneacetone)dipalladium (Pd₂(dba)₃), a compound having a structure of following Formula (a), triethylamine, and N,N-dimethylformamide (DMF) to conduct a Sonogashira coupling reaction, so as to obtain a compound having a structure of following Formula (V);

Formula (a)

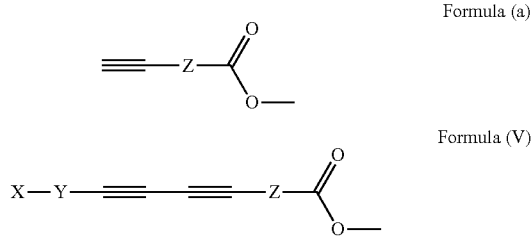

Formula (V)

mixing the compound of Formula (V) with tetrahydrofuran (THF) and a sodium hydroxide (NaOH) solution to conduct a hydrolysis reaction, so as to obtain a compound having a structure of following Formula (VI);

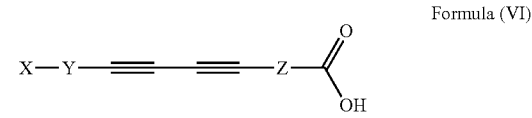

Formula (VI)

mixing the compound of Formula (VI) with (S)-methyl 2-amino-3-((tert-butoxycarbonyl)amino)-3-methylbutanoate, diisopropylethylamine (DIPEA), O-(7-azabenzotriazol-1-yl)-N,N,N',N'-tetramethyluronium hexafluorophosphate (HATU), and N,N-dimethylformamide (DMF) to conduct a condensation reaction, so as to obtain a compound having a structure of following Formula (VII);

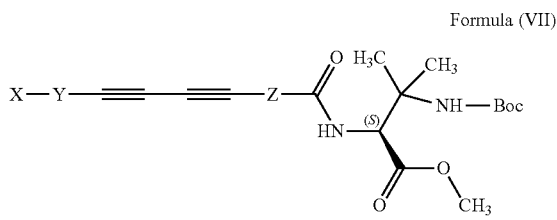

Formula (VII)

mixing the compound of Formula (VII) with methanol and hydrogen chloride gas to conduct a Boc-deprotection reaction, so as to obtain a compound having a structure of following Formula (VIII); and

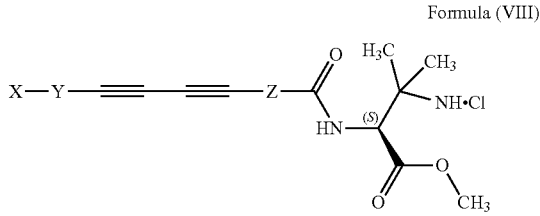

Formula (VIII)

mixing the compound of Formula (VIII) with isopropanol and an aqueous solution of hydroxylamine to conduct a substitution reaction, so as to obtain the compound of Formula (I).

In a preferred embodiment, the molar ratio of the Dess-Martin periodinane to the compound of Formula (II) is 1.0 to 1.2.

In a preferred embodiment, the oxidation reaction is conducted at room temperature for 2 to 8 hours.

In a preferred embodiment, the molar ratio of the compound of Formula (III)/triphenylphosphine/carbon tetrabromide is 1:(3.8-4.2):(1.8-2.2).

In a preferred embodiment, the Corey-Fuchs reaction is conducted at a temperature of −20 to −78° C.

In a preferred embodiment, the molar ratio of the compound of Formula (IV)/Pd₂(dba)₃/the compound of Formula (a)/triethylamine is 1:(0.02-0.04):(1.8-2.2):(2.8-3.2).

In a preferred embodiment, the Sonogashira coupling reaction is conducted at a temperature of 75 to 85° C. for 6 to 10 hours.

In a preferred embodiment, the molar ratio of sodium hydroxide in the sodium hydroxide solution to the compound of Formula (V) is 8 to 12.

In a preferred embodiment, the hydrolysis reaction is conducted at room temperature for 6 to 10 hours.

In a preferred embodiment, the molar ratio of the compound of Formula (VI)/(S)-methyl 2-amino-3-((tert-butoxycarbonyl)amino)-3-methylbutanoate/DIPEA/HATU is 1:(1.1~1.3):(3.8~4.2):(1.1~1.3).

In a preferred embodiment, the condensation reaction is conducted at room temperature for 3 to 8 hours.

In a preferred embodiment, the molar ratio of hydroxylamine in the aqueous solution of hydroxylamine to the compound of Formula (VIII) is 18 to 22.

A further aspect of the present disclosure provides the use of the hydroxamic acid derivative as described above or produced according to the method as described above in inhibition of UDP-3-O—(R-3-hydroxymyristol)-N-acetyl-glucosamine deacetylase (LpxC).

In contrast to prior art, the hydroxamic acid group of the hydroxamic acid derivative of Formula (I) according to the present disclosure can be chelated with zinc ions in the LpxC active area, and the derivative has a hydrophobic side chain which can bind to hydrophic channels in the enzyme LpxC. These guarantee that the hydroxamic acid derivative according to the disclosure has good bactericidal activity against Gram-negative bacteria and low toxicity.

The present disclosure also provides a method for producing the hydroxamic acid derivative, which requires a shorter reaction time and can provide the derivative with a high yield.

DETAILED DESCRIPTION
Embodiments of the present disclosure will now be described in further detail.
One aspect of the disclosure provides a hydroxamic acid derivative having a structure of following Formula (I):
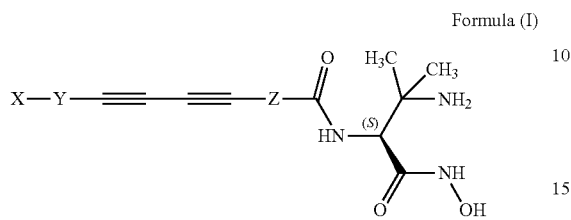
Formula (I)
where,
X is
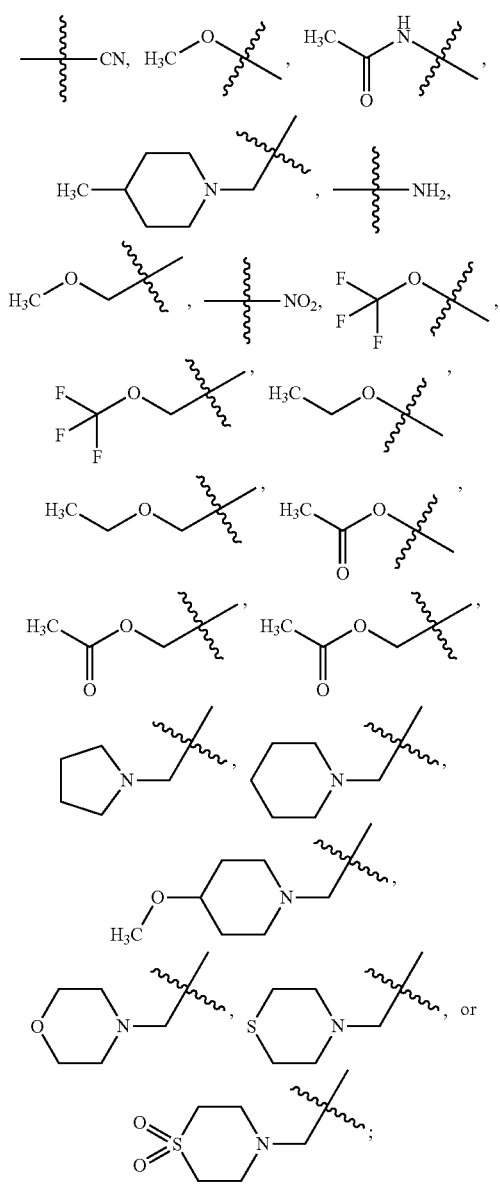
Y is
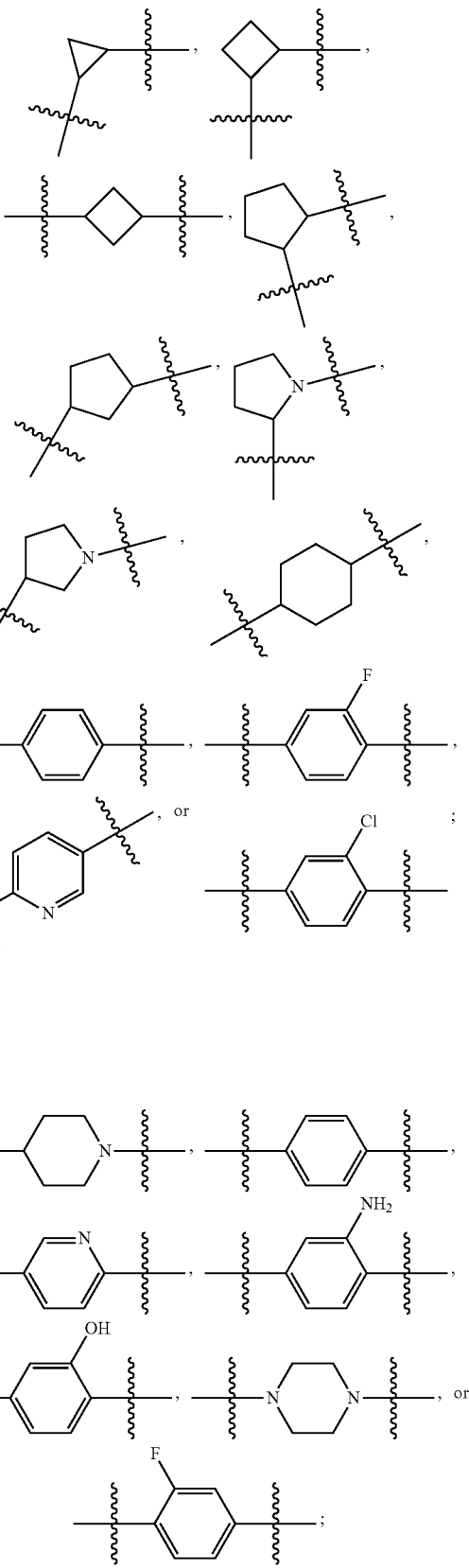
and
Z is where, when Y and Z are

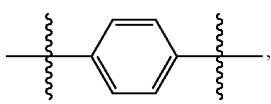

X is not

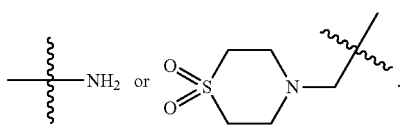

In a preferred embodiment, X is

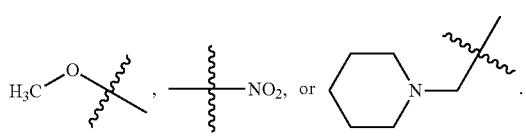

In a preferred embodiment, Y is

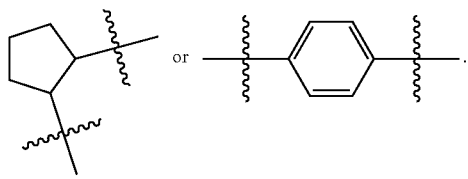 [SMILES: *C1CCCC1* ; *c1ccc(*)cc1]

In a preferred embodiment, Z is

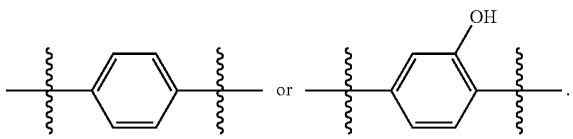 [SMILES: *c1ccc(*)cc1 ; *c1ccc(*)c(O)c1]

In a further preferred embodiment, the hydroxamic acid derivative is N—((S)-3-amino-1-(hydroxyamino)-3-methyl-1-oxobutan-2-yl)-4-(((1R,2S)-2-methoxycyclopentyl)butan-1,3-diyne-1-yl)benzamide, (S)—N-(3-amino-1-(hydroxyamino)-3-methyl-1-oxobutan-2-yl)-4-((4-nitrophenyl) butan-1,3-diyne-1-yl)-piperazin-1-carboxamide, or (S)—N-(3-amino-1-(hydroxyamino)-3-methyl-1-oxobutan-2-yl)-2-hydroxy-4-((4-(piperidin-1-ylmethyl)phenyl)butan-1,3-diyne-1-yl)benzamide.

Another aspect of the disclosure provides a method for producing the hydroxamic acid derivative as described above, including steps of:

mixing a compound having a structure of following Formula (II) with Dess-Martin periodinane and dichloromethane to conduct an oxidation reaction, so as to obtain a compound having a structure of following Formula (III);

Formula (II)

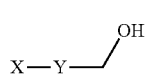

Formula (III)

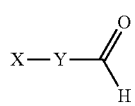

mixing the compound of Formula (III) with triphenylphosphine, carbon tetrabromide (CBr₄), and dichloromethane to conduct the Corey-Fuchs reaction, so as to obtain a compound having a structure of following Formula (IV);

Formula (IV)

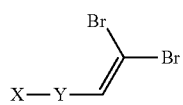

mixing the compound of Formula (IV) with tris(dibenzylideneacetone)dipalladium (Pd₂(dba)₃), a compound having a structure of following Formula (a), triethylamine, and N,N-dimethylformamide (DMF) to conduct a Sonogashira coupling reaction, so as to obtain a compound having a structure of following Formula (V);

Formula (a)

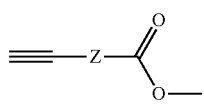

Formula (V)

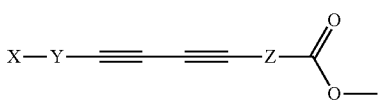

mixing the compound of Formula (V) with tetrahydrofuran (THF) and a sodium hydroxide (NaOH) solution to conduct a hydrolysis reaction, so as to obtain a compound having a structure of following Formula (VI);

Formula (VI)

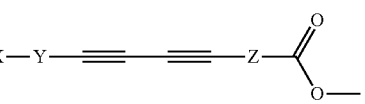

mixing the compound of Formula (VI) with (S)-methyl 2-amino-3-((tert-butoxycarbonyl)amino)-3-methylbutanoate, diisopropylethylamine (DIPEA), O-(7-azabenzotriazol-1-yl)-N,N,N',N'-tetramethyluronium hexafluorophosphate (HATU), and N,N-dimethylformamide (DMF) to conduct a condensation reaction, so as to obtain a compound having a structure of following Formula (VII);

Formula (VII)

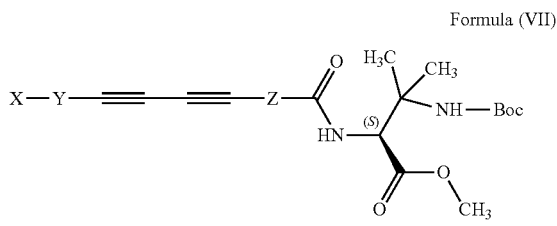

mixing the compound of Formula (VII) with methanol and hydrogen chloride gas to conduct a Boc-deprotection reaction, so as to obtain a compound having a structure of following Formula (VIII); and Formula (VIII)

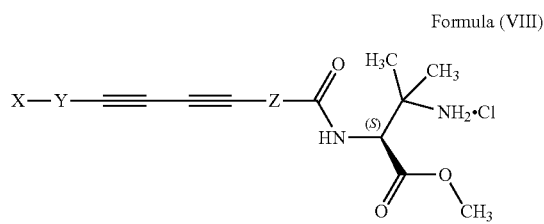

mixing the compound of Formula (VIII) with isopropanol and an aqueous solution of hydroxylamine to conduct a substitution reaction, so as to obtain the compound of Formula (I).

In the embodiments of the present disclosure, the starting materials used in the method may be any commercially available materials or products well known to those skilled in the art unless otherwise specified.

According to the method, the compound of Formula (II) is mixed with Dess-Martin periodinane and dichloromethane for an oxidation reaction, so as to obtain the compound of Formula (III).

In an embodiment where X is

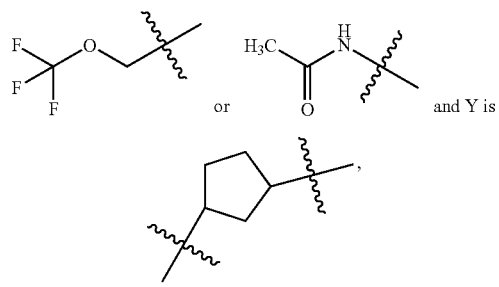

the compound of Formula (II) is preferably produced from

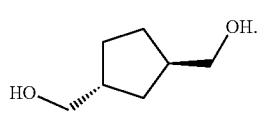

In a further embodiment where X is

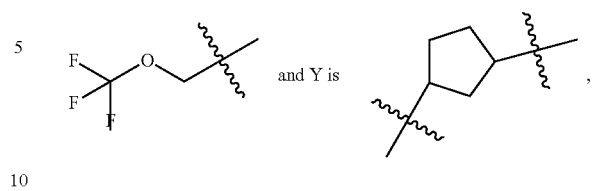

the compound of Formula (II) is preferably produced according to the following Scheme 1.

Scheme 1

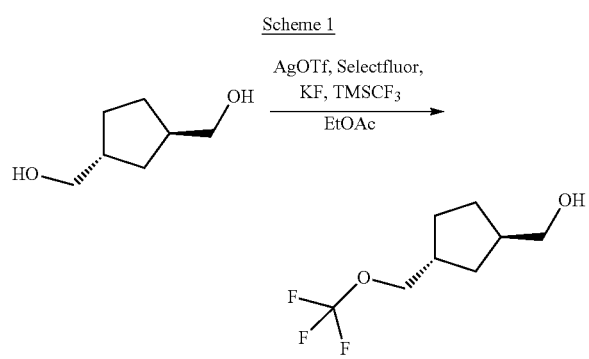

In particular, in this embodiment, the compound of Formula (II) may be produced by mixing AgOTf (12.8 g, 50 mmol), Selectfluor (8.9 g, 25 mmol), and potassium fluoride (3.9 g, 66 mmol) in ethyl acetate (30 ml) under argon atmosphere; adding to the mixture

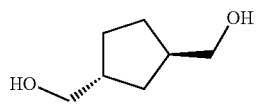

(6.5 g, 50 mmol) and trimethyl(trifluoromethyl)silane (7.1 g, 50 mmol) to conduct a reaction at room temperature for 8 h; and subjecting the reaction mixture after this reaction to filtration and concentration, so as to obtain a crude product, which is then purified using silica gel column chromatography (PE:EA=20:1-10:1) to obtain the final product, i.e.,

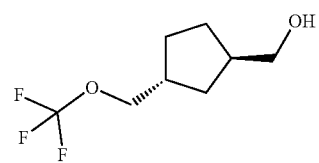 [SMILES: OC[C@@H]1CC[C@@H](COC(F)(F)F)C1]

(4.3 g, 43%).

In another embodiment where X is and Y is

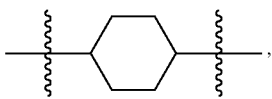 [SMILES: *C1CCC(*)CC1]

the compound of Formula (II) is preferably produced from

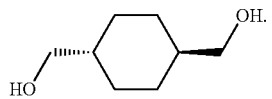

In this embodiment, the compound of Formula (II) is preferably produced according to the following Scheme 2.

Scheme 2

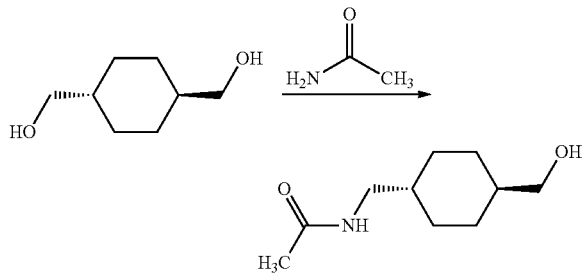

In particular, in this embodiment, the compound of Formula (II) may be produced by mixing acetamide (1.0 g, 17 mmol),

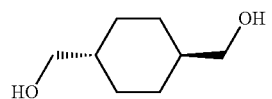

(7.3 g, 51 mmol), and pentamethylcyclopentadienyliridium (iii) chloride (0.3 g, 0.4 mmol) into a microwave reaction tube to conduct a microwave reaction at 130° C. for 3 h; allowing the reaction mixture after this reaction to cool to room temperature, followed by addition of water (10 ml) and extraction (preferably 3 times) with ethyl acetate (the ratio of water to ethyl acetate being preferably 1.0 to 1.5); and combining organic phases, followed by drying over anhydrous sodium sulfate, filtration and concentration, to give a crude product, which is then purified using silica gel column chromatography (DCM:MeOH=20:1) to obtain the final product (0.9 g, 30%).

In a further embodiment where X is

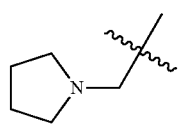 [SMILES: *CN1CCCC1]

and Y is

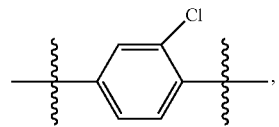

the compound of Formula (II) is preferably produced from

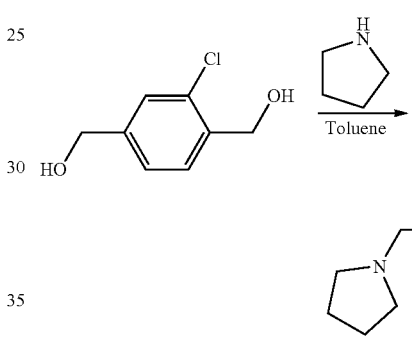

In this embodiment, the compound of Formula (II) is preferably produced according to the following Scheme 3.

Scheme 3

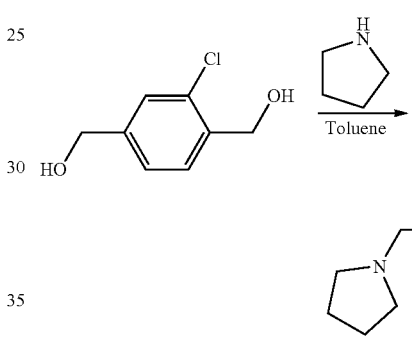

In particular, in this embodiment, the compound of Formula (II) may be produced by adding D(+)-10-camphorsulfonic acid (0.9 g, 4 mol) to pyrrolidine (0.7 g, 10 mmol) in toluene (10 ml), followed by stirring at room temperature for 1 min; adding to the mixture (4.3 g, 25 mmol) and a ruthenium-NHC complex (0.1 mmol), followed by stirring at 120° C. for 10 h; allowing the reaction mixture after reaction to cool to room temperature, followed by addition of water (the ratio of toluene to water being preferably 1.0 to 1.5), and extraction (preferably 3 times) with ethyl acetate (the ratio of water to ethyl acetate being preferably 1.0 to 1.5); and combining organic phases, followed by drying over anhydrous sodium sulfate, filtration and concentration, to give a crude product, which is then purified using silica gel column chromatography (PE:EA=20:1-10:1) to obtain the final product (0.8 g, 37%).

In other embodiments where the compound of Formula (II) has a structure different from the above three structures, it is commercially available or can be prepared according to any known method.

The molar ratio of Dess-Martin periodinane to the compound of Formula (II) is preferably 1.0 to 1.5, more preferably 1.2 to 1.3. The ratio of the compound of Formula (II) to dichloromethane is preferably 1 g:(15-30) ml, more preferably 1 g:(18-28) ml, and most preferably 1 g:(21-25) ml.

According to an embodiment of the disclosure, the step of mixing the compound of Formula (II) with Dess-Martin periodinane and dichloromethane preferably comprises: mixing the compound of Formula (II) with dichloromethane at −10° C. to form a dichloromethane solution of the compound of Formula (II); and adding thereto Dess-Martin periodinane in portions (the temperature of the reaction mixture would rise during the addition, and may be maintained at −7 to −10° C. by controlling the addition rate).

According to an embodiment of the disclosure, the oxidation reaction is conducted while stirring is performed. The stirring process is not particularly limited, and may be performed in any suitable manner known to those skilled in the art. The oxidation reaction may be performed preferably at room temperature for preferably 2 to 8 hours, more preferably 4 to 6 hours.

Preferably, the method of the disclosure further comprises: after completion of the oxidation reaction, subjecting the reaction mixture to a post-treatment step. The post-treatment preferably comprises: quenching the reaction mixture by addition of saturated aqueous sodium thiosulfate and saturated aqueous sodium hydrogen carbonate after the reaction mixture is transferred to an ice bath; filtrating the quenched mixture to remove solids; allowing the resulting filtrate to stand for layer separation, so as to form an organic phase and an aqueous phase which is extracted three times using dichloromethane; and combining the organic phases, followed by drying over anhydrous sodium sulfate, filtration, concentration under reduced pressure, and purification using silica gel column chromatography (eluent: petroleum ether/ethyl acetate=20:1).

According to the method of the disclosure, after the compound of Formula (III) is obtained, it is mixed with triphenylphosphine, carbon tetrabromide ($CBr_4$), and dichloromethane to conduct the Corey-Fuchs reaction, so as to obtain the compound of Formula (IV). The molar ratio of the compound of Formula (III):triphenylphosphine:carbon tetrabromide is preferably 1:(3.8-4.2):(1.8-2.2), more preferably 1:(3.9-4.1):(1.9-2.1). The ratio of the compound of Formula (III) to the first organic solvent is preferably 1 g:(25-45) ml, more preferably 1 g:(30-40) ml, and most preferably 1 g:(34-36) ml.

According to an embodiment of the disclosure, the step of mixing the compound of Formula (III) with triphenylphosphine, carbon tetrabromide, and dichloromethane preferably comprises:

mixing the compound of Formula (III) with a first portion of a first organic solvent to form a solution of the compound of Formula (III);

mixing triphenylphosphine with a second portion of the first organic solvent to form a solution of triphenylphosphine;

mixing carbon tetrabromide with a third portion of the first organic solvent to form a solution of carbon tetrabromide; and mixing the solution of carbon tetrabromide, the solution of triphenylphosphine, and the solution of the compound of Formula (III).

The amount of the first, second, or third portion of the first organic solvent is not particularly limited as long as the corresponding solutes can be dissolved completely. The sum of the first, second, and third portions of the first organic solvent is equal to the amount of the first organic solvent used.

According to a particular embodiment, the step of mixing the carbon tetrabromide solution, the triphenylphosphine solution, and the solution of the compound of Formula (III) preferably comprises: adding the triphenylphosphine solution dropwise to the carbon tetrabromide solution to conduct a reaction while stirring the mixture at −20° C. under argon atmosphere; cooling the reaction mixture after reaction to −78° C.; and adding thereto the solution of the compound of Formula (III) dropwise, followed by further stirring for 30 minutes to conduct a further reaction.

The dropwise addition is not particularly limited, and may be carried out in any suitable manner known to those skilled in the art. Similarly, the stirring process is not particularly limited, and may be carried out in any suitable manner known to those skilled in the art.

During the course of the reaction, the triphenylphosphine can attack carbon tetrabromide ($CBr_4$) and abstract one bromide ion therefrom to generate phosphonium ions and $Br_3C^-$ ions. A phosphorus ylide is then generated through a nucleophilic substitution of the phosphonium ions by the $Br_3C^-$ ions that are produced simultaneously with the phosphonium ions. Thereafter, a nucleophilic addition of the phosphorus ylide to an aldehyde is conducted to generate an amphoteric intermediate, which is cyclized to an oxetane with one carbon in the ring being replaced by phosphorus, which further reduces triphenylphosphine oxide and dibromoolefin then.

In a preferred embodiment, the Corey-Fuchs reaction is conducted while stirring is performed. The stirring process is not particularly limited, and may be carried out in any suitable manner well known to those skilled in the art. The Corey-Fuchs reaction may be performed at preferably −20 to −78° C., more preferably −60 to −70° C., for preferably 20 to 40 minutes, more preferably 25 to 35 minutes. In the embodiments of the disclosure, the reaction time is started when the addition of the compound of Formula (III) is complete.

Preferably, the method of the disclosure further comprises: after completion of the Corey-Fuchs reaction, subjecting the reaction mixture to a post-treatment step. The post-treatment preferably comprises: allowing the reaction mixture to rise to room temperature; removing the solvent from the mixture by distillation under reduced pressure; adding to the residue a 40% ethanol solution and n-hexane, followed by vigorous stirring for 10 minutes and then settling for layer separation; and subjecting the n-hexane layer to concentration under reduced pressure. The resulting concentrate can be directly used in the next reaction without purification.

According to the method of the disclosure, after the compound of Formula (IV) is obtained, it is mixed with $Pd_2(dba)_3$, the compound of Formula (a), triethylamine, and DMF to conduct a Sonogashira coupling reaction, so as to obtain the compound of Formula (V).

The molar ratio of the compound of Formula (IV):$Pd_2(dba)_3$:the compound of formula (a):triethylamine is preferably 1:(0.02-0.04):(1.8-2.2):(2.8-3.2), more preferably 1:(0.025-0.035):(1.9-2.1):(2.96-3.1). The ratio of the compound of Formula (IV) to DMF is preferably 1 g:(10-18) ml, more preferably 1 g:(12-16) ml, and most preferably 1 g:(13-15) ml.

According to an embodiment of the disclosure, the mixing is preferably performed under argon atmosphere. The mixing process is not particularly limited, and may be carried out in any suitable manner well known to those skilled in the art.

According to an embodiment of the disclosure, the Sonogashira coupling reaction is preferably conducted while stirring is performed. The stirring process is not particularly limited, and may be carried out in any suitable manner well known to those skilled in the art. The Sonogashira coupling reaction may be conducted at preferably 75 to 85° C., more preferably 78 to 82° C., for preferably 6 to 10 hours, more preferably 8 to 9 hours.

According to the method of the disclosure, $Pd_2(dba)_3$ serves as a catalyst, triethylamine serves as an acid-binding agent, and DMF serves as a solvent.

According to an embodiment of the disclosure, the method further comprises: after completion of the Sonogashira coupling reaction, subjecting the reaction mixture to a post-treatment step. The post-treatment preferably comprises: adding ethyl acetate to the reaction mixture, followed by washing three times using water, drying over anhydrous sodium sulfate, filtration, concentration under reduced pressure, and purification using silica gel column chromatography (eluent: petroleum ether/ethyl acetate=80:1).

According to the method of the disclosure, after the compound of Formula (V) is obtained, it is mixed with THE and a NaOH solution to conduct a hydrolysis reaction, so as to obtain the compound of Formula (VI). The NaOH solution is preferably an aqueous NaOH solution, with the ratio of NaOH to water being preferably 0.15-0.25 g:1 ml, more preferably 0.18-0.22 g:1 ml.

According to an embodiment of the disclosure, the step of mixing the compound of Formula (V) with THE and the NaOH solution preferably comprises:

mixing the compound of Formula (V) with THE to form a THE solution of the compound of Formula (V), which is then mixed with the NaOH solution. The mixing process is not particularly limited, and may be carried out in any suitable manner well known to those skilled in the art.

The molar ratio of NaOH in the NaOH solution to the compound of Formula (V) is preferably 8 to 12, more preferably 9 to 11. The ratio of the compound of Formula (V) to THF is preferably 1 g:(15-40) ml, more preferably 1 g:(20-30) ml, and most preferably 1 g:(35-37) ml.

Preferably, the hydrolysis reaction is conducted while stirring is performed. The stirring process is not particularly limited, and may be carried out in any suitable manner well known to those skilled in the art. The hydrolysis reaction may be conducted preferably at room temperature for preferably 6 to 10 hours, more preferably for 8 to 9 hours.

According to an embodiment, the method further comprises: after completion of the hydrolysis reaction, subjecting the reaction mixture to a post-treatment step. The post-treatment preferably comprises: removing the solvent from the reaction mixture by distillation under reduced pressure; adding water to the residue, followed by pH adjustment to 2.0 with a 1 mol/L hydrochloric acid solution and extraction using ethyl acetate; and combining organic phases, followed by drying over anhydrous sodium sulfate, filtration, and concentration under reduced pressure. The resulting concentrate can be directly used in the next reaction without purification.

According to the method of the disclosure, after the compound of Formula (VI) is obtained, it is mixed with (S)-methyl 2-amino-3-((tert-butoxycarbonyl)amino)-3-methylbutanoate, DIPEA, HATU, and DMF to conduct a condensation reaction, so as to obtain the compound of Formula (VII).

Preferably, the step of mixing the compound of Formula (VI) with (S)-methyl 2-amino-3-((tert-butoxycarbonyl)amino)-3-methylbutanoate, DIPEA, HATU, and DMF comprises:

mixing the compound of Formula (VI) with HATU and DMF to form a solution (the mixing process is not particularly limited, and may be carried out in any suitable manner well known to those skilled in the art); and adding to the solution (S)-methyl 2-amino-3-((tert-butoxycarbonyl)amino)-3-methylbutanoate (Boc-S) and DIPEA and mixing (the mixing process is not particularly limited, and may be carried out in any suitable manner well known to those skilled in the art).

The molar ratio of the compound of Formula (VI):Boc-S:DIPEA:HATU is preferably 1:(1.1-1.3):(3.8-4.2):(1.1-1.3), more preferably 1:(1.15-1.25):(3.9-4.1):(1.15-1.25). The ratio of the compound of Formula (VI) to DMF is preferably 1 g:(15-30) ml, more preferably 1 g:(17-28) ml, and most preferably 1 g:(20-25) ml.

The condensation reaction is preferably conducted while stirring is performed. The stirring process is not particularly limited, and may be carried out in any suitable manner well known to those skilled in the art. The condensation reaction may be conducted preferably at room temperature for preferably 3 to 8 hours, more preferably 4 to 6 hours.

According to the method of the disclosure, HATU serves to activate carboxyl groups, and DIPEA serves to activate amino groups.

According to an embodiment of the disclosure, the method further comprises: after completion of the condensation reaction, subjecting the reaction mixture to a post-treatment step. The post-treatment preferably comprises: adding ethyl acetate to the reaction mixture, followed by washing three times with an aqueous 1.2 mol/L lithium chloride solution, drying of the organic phase over anhydrous sodium sulfate, filtration, concentration under reduced pressure, and purification using silica gel column chromatography (eluent: petroleum ether/ethyl acetate=2:1)

According to the method of the disclosure, after the compound of Formula (VII) is obtained, it is mixed with methanol and hydrogen chloride gas to conduct a Boc-deprotection reaction, so as to obtain the compound of Formula (VIII).

According to an embodiment of the disclosure, the step of mixing the compound of Formula (VII) with methanol and hydrogen chloride gas preferably comprises: mixing the compound of Formula (VII) with methanol; and introducing thereinto the hydrogen chloride gas. The mixing process is not particularly limited, and may be carried out in any suitable manner well known to those skilled in the art. The hydrogen chloride gas may be introduced into the mixture of the compound of Formula (VII) and methanol at a rate of preferably 0.5 mL/s, more preferably 1 mL/s, for preferably 15 to 25 minutes, more preferably 18 to 22 minutes, and most preferably 20 minutes. In an embodiment, the Boc-deprotection reaction is conducted with a reaction time equal to the gas-introduction time period. In an embodiment, the Boc-deprotection reaction may be conducted preferably at room temperature.

According to an embodiment of the disclosure, the method further comprises: after completion of the Boc-deprotection reaction, subjecting the reaction mixture to a post-treatment step. The post-treatment preferably comprises removing the solvent from the reaction mixture by distillation under reduced pressure to give a crude product of the compound of Formula (VIII). This crude product can be directly used in the next reaction without purification.

According to the method of the disclosure, after the compound of Formula (VIII) is obtained, it is mixed with isopropanol and an aqueous solution of hydroxylamine to conduct a substitution reaction, so as to obtain the compound of Formula (I). The aqueous solution of hydroxylamine may have a concentration of preferably 16 to 17 mmol/mL, more preferably 16.5 to 16.8 mmol/mL.

According to an embodiment of the disclosure, the step of mixing the compound of Formula (VIII) with isopropanol and the aqueous solution of hydroxylamine preferably comprises: mixing the compound of Formula (VIII) with isopropanol, followed by mixing with the aqueous solution of hydroxylamine. The mixing process is not particularly limited, and may be carried out in any suitable manner well known to those skilled in the art.

The molar ratio of hydroxylamine in the aqueous solution of hydroxylamine to the compound of Formula (VIII) is preferably 18 to 22, more preferably 19 to 21, and most preferably 20. The ratio of the compound of Formula (VIII) to isopropanol is preferably 1 g:(20-30) ml, more preferably 1 g:(22-28) ml, and most preferably 1 g:(24-26) ml.

The substitution reaction is preferably conducted while stirring is performed. The stirring process is not particularly limited, and may be carried out in any suitable manner well known to those skilled in the art. The substitution reaction is preferably conducted at room temperature. Preferably, the progress of the substitution reaction is monitored by LCMS to determine whether this reaction is completed.

According to an embodiment of the disclosure, the method further comprises: after completion of the substitution reaction, subjecting the reaction mixture to a post-treatment step. The post-treatment preferably comprises purifying the reaction mixture by reverse-phase HPLC (chromatography column: XDB-C18 (21.2×250 mm, 7 μm); mobile phase A: acetonitrile (containing 0.1% TFA), mobile phase B: water (containing 0.1% TFA); gradient elution: 5 to 30% A from 0 to 40 minutes; column temperature: 25° C.; flow rate: 10 ml/min; detection wavelength: 280 nm), followed by freeze drying.

A further aspect of the disclosure provides the use of the hydroxamic acid derivative as described above or produced according to the method as described above in inhibition of LpxC.

The embodiments of the disclosure will now be further described by way of the following examples. However, these examples should not be construed as limiting the scope of the disclosure.

EXAMPLES

Example 1

N—((S)-3-amino-1-(hydroxyamino)-3-methyl-1-oxobutan-2-yl)-4-(((1R,2S)-2-methoxycyclopentyl)butan-1,3-diyne-1-yl)benzamide was prepared according to the following Scheme 4.

Scheme 4

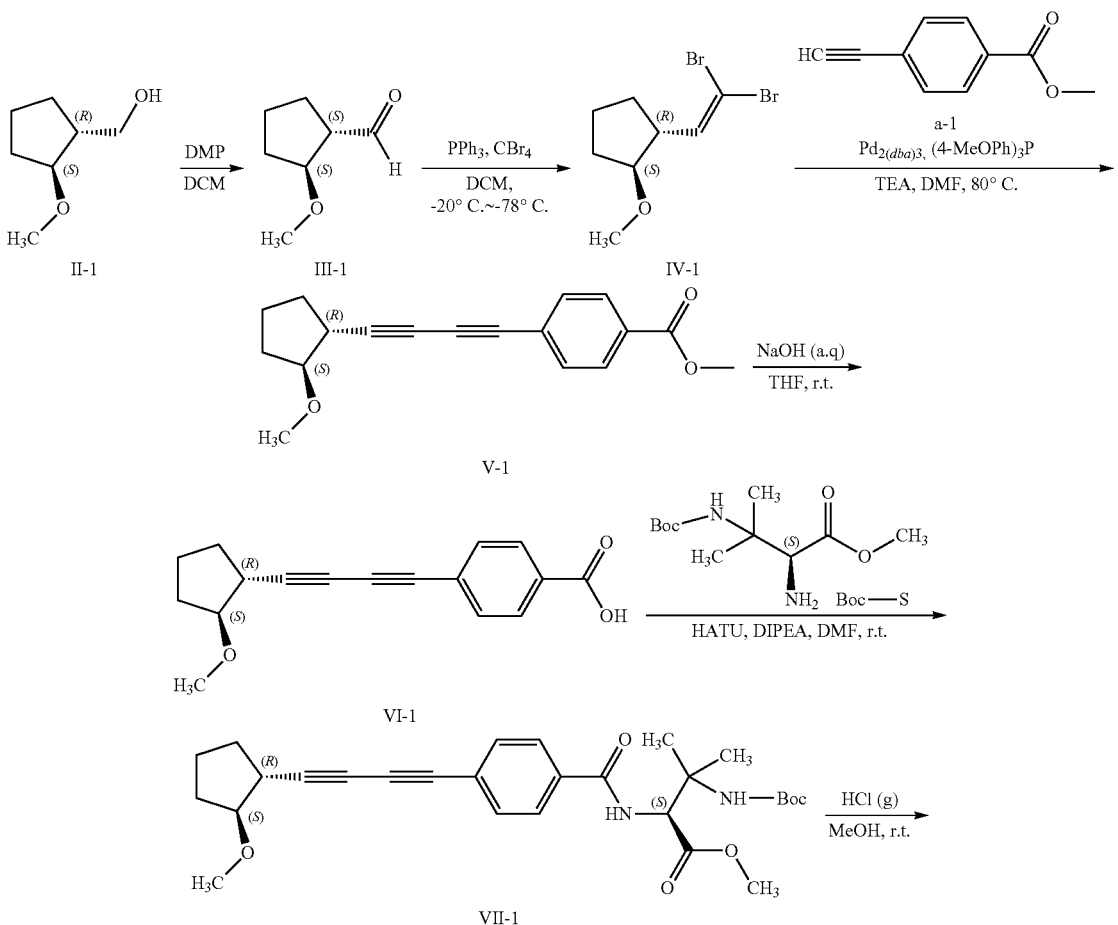

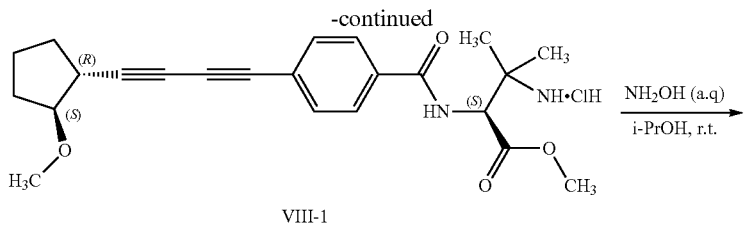

VIII-1

I-1

Preparation of (1S,2S)-2-methoxycyclopentyl-1-carbaldehyde (III-1)

Dess-Martin periodinane (30.96 g, 73 mmol) was added in portions to a solution of the compound II-1 (8.85 g, 68 mmol) in dichloromethane (250 ml) at −10° C. The addition rate of Dess-Martin periodinane was controlled such that the temperature of the reaction mixture was maintained at −7 to −10° C. On completion of addition, the reaction mixture was stirred at room temperature for 4 h. After the reaction, the reaction mixture was transferred to an ice bath and quenched by addition of saturated aqueous sodium thiosulfate (100 mL) and saturated aqueous sodium hydrogen carbonate (250 mL). The quenched reaction mixture was filtrated to remove solids. The filtrate was allowed to stand for layer separation, and the aqueous layer obtained was extracted 3 times using dichloromethane (100 mL*3). The organic phases obtained were combined and dried over anhydrous sodium sulfate, followed by filtration, concentration under reduced pressure, and purification using silica gel column chromatography (eluent: petroleum ether/ethyl acetate=20:1) to obtain the compound III-1 (6.02 g, 69.13%). MS-APCI (m/z): 129.1 [M+H]$^+$

Preparation of (1R,2S)-1-(2,2-dibromovinyl)-2-methoxy Cyclopentane (IV-1)

A solution of triphenylphosphine (39.09 g, 149 mmol) in DCM (75 ml) was added dropwise to a solution of carbon tetrabromide (24.71 g, 75 mmol) in DCM (60 ml) at −20° C. under argon atmosphere. On completion of addition, the mixed solution was allowed to react while stirred for 30 min. The resulting reaction mixture was cooled to −78° C., and then a solution of the compound III-1 (4.75 g, 37 mmol) in DCM (60 ml) was added thereto. On completion of addition, the reaction mixture was allowed to react while stirred for 30 min. Thereafter, the reaction mixture after the reaction was allowed to warm to room temperature. The solvent was then distilled off under reduced pressure, and the residue was dissolved in 40% ethanol solution to give a yellow liquid. To the liquid, n-hexane was added, and the mixture was stirred vigorously for 10 min and then was allowed to stand for layer separation. The n-hexane layer obtained was concentrated under reduced pressure to obtain a crude compound IV-1 (9.2 g, 88.2%), which was directly used in the next reaction without purification. A small amount of the crude compound IV-1 was purified using silica gel column chromatography (eluent: petroleum ether/ethyl acetate=150:1) to give a yellow oil. The structure of the oil was then confirmed. MS-ESI (m/z): 304.9[M+Na]$^+$

Preparation of 4-(((1R,2S)-2-methoxycyclopentyl) butan-1,3-diyne-1-yl)benzoic Acid Methyl Ester (V-1)

To DMF (100 ml), the compound IV-1 (6.00 g, 21 mmol), methyl 4-ethynylbenzoate (a-1) (6.89 g, 43 mmol), Pd$_2$(dba)$_3$ (0.58 g, 0.63 mmol), (4-MeOPh)$_3$P (0.44 g, 1.26 mmol), and triethylamine (6.37 g, 63 mmol) were added. The mixture was allowed to react at 80° C. for 8 h. After the reaction, ethyl acetate (300 L) was added thereto, and the mixture was washed using water (150 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=80:1) to obtain the compound V-1 (2.38 g, 40.16%). MS-ESI (m/z): 283.1[M+H]$^+$

Preparation of 4-(((1R,2S)-2-methoxycyclopentyl) butan-1,3-diyne-1-yl)benzoic Acid (VI-1)

To a solution of the compound V-1 (1.70 g, 6 mmol) in THE (60 ml), a solution of NaOH (2.40 g, 60 mmol) in water (10 ml) was added. The mixed solution was allowed to react at room temperature while stirred for 8 h. The solvent was distilled off under reduced pressure. To the residue water (50 ml) was added, and then a 1 mol/L aqueous solution of hydrochloric acid was added thereto to adjust its pH to a value of around 2.0. The resulting mixture was extracted using ethyl acetate (50 ml*4). The organic phases obtained were combined and dried over anhydrous sodium sulfate, followed by filtration and concentration under reduced pressure to give the crude compound VI-1 (1.39 g, 86.1%), which was directly used in the next reaction without purification. A small amount of the crude compound VI-1 was purified to give a pale yellow solid. The structure of the solid was then confirmed. MS-ESI (m/z): 267.1[M−H]$^-$

Preparation of (S)-3-((tert-butoxycarbonyl)amino)-2-(4-(((1R,2S)-2-methoxycyclopentyl)butan-1,3-diyne-1-yl)benzoylamino)-3-ylbutyrate (VII-1)

To a solution of the compound of (VI-1) (5.30 g, 19.7 mmol) and HATU (9.21 g, 23.6 mmol) in DMF, (S)-2- amino-3-(tert-butoxycarbonylamino)-3-methyl-butyric acid methyl ester (Boc-S) (5.81 g, 23.6 mmol) and DIPEA (10.18 g, 78.8 mmol) were added. The mixture was allowed to react at room temperature while stirred for 5 h. After the reaction, ethyl acetate (300 ml) was added thereto. The resulting mixture was washed using an aqueous 1.2 mol/L lithium chloride solution (100 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=2:1) to obtain the compound VII-1 (6.87 g, 70.3%). MS-ESI (m/z): 497.3[M+H]$^+$)

Preparation of (S)-3-amino-2-(4-(((1R,2S)-2-methoxycyclopentyl)butan-1,3-diyne-1-yl)benzoylamino)-3-methyl-butyric Acid Methyl Ester (VIII-1)

The compound VII-1 (6.70 g, 13.5 mmol) was dissolved in methanol (30 ml), and dry hydrogen chloride gas was then introduced into the solution for 20 min. After reaction, the solvent was distilled off under reduced pressure to give the compound VIII-1 (4.96 g, 93.0%), which was directly used in the next reaction without purification. MS-ESI (m/z): 396.5[M+H]$^+$

Preparation of N—((S)-3-amino-1-(hydroxyamino)-3-methyl-1-oxobutan-2-yl)-4-(((1R,2S)-2-methoxycyclopentyl)butan-1,3-diyne-1-yl)benzamide (I-1)

The compound VIII-1 (4.15 g, 10.5 mmol) was dissolved in a mixture of isopropanol (12 ml) and a 16.85 mol/L aqueous hydroxylamine solution (12.5 ml, 210 mmol). The resulting solution was allowed to react at room temperature while stirred until LCMS indicated that the reaction was complete. The reaction mixture after the reaction was purified using reverse HPLC (chromatography column: XDB-C18 (21.2×250 mm, 7 µm), mobile phase A: acetonitrile (containing 0.1% TFA), mobile phase B: water (containing 0.1% TFA), gradient elution: 5 to 30% A from 0 to 40 minutes; column temperature: 25° C.; flow rate: 10 ml/min; detection wavelength: 280 nm), followed by freeze drying, to give the crude compound I-1 (2.19 g, 52.5%). MS-ESI (m/z) 398.2[M+H]$^+$. $^1$H NMR (500 MHz, CDCl$_3$) δ 9.10 (d, J=4.0 Hz, 1H), 8.83 (d, J=4.0 Hz, 1H), 8.45 (d, J=10.6 Hz, 1H), 7.78-7.72 (m, 2H), 7.57-7.54 (m, 2H), 4.34 (d, J=10.6 Hz, 1H), 3.80-3.73 (m, 1H), 3.28 (d, J=1.4 Hz, 3H), 2.95-2.88 (m, 1H), 2.43 (s, 1H), 1.87-1.79 (m, 1H), 1.79-1.64 (m, 3H), 1.23 (s, 2H), and 1.17 (s, 2H).

Example 2

(S)—N-(3-amino-1-(hydroxyamino)-3-methyl-1-oxobutan-2-yl)-4-((4-nitrophenyl)butan-1,3-diyne-1-yl)-piperazin-1-carboxamide (I-2) was prepared according to the following Scheme 5.

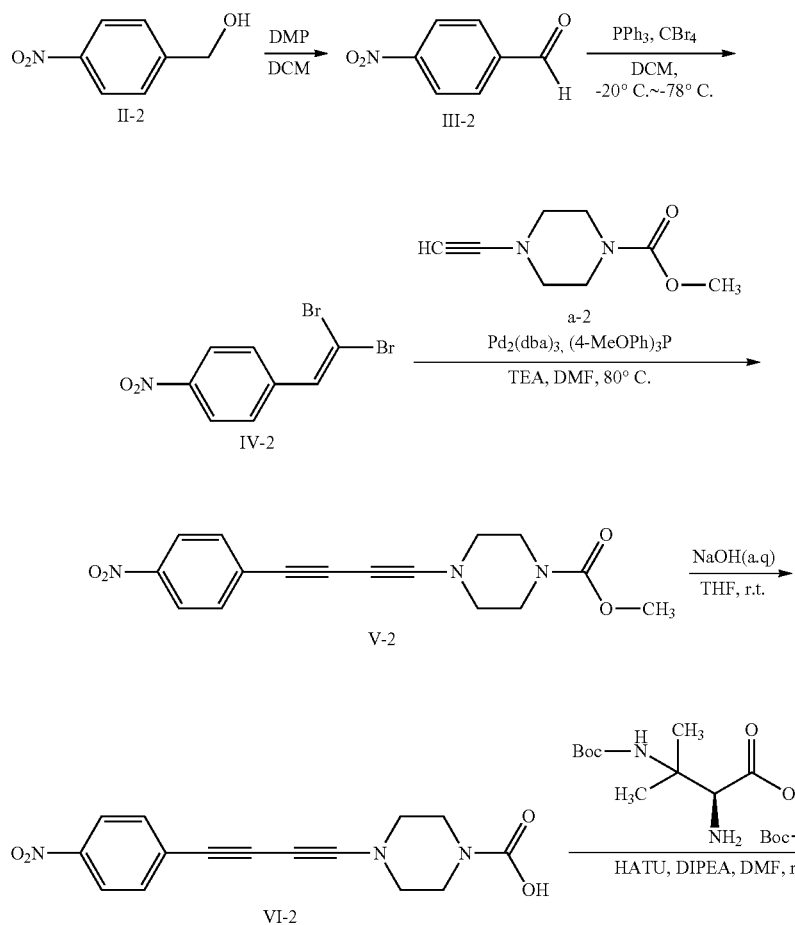

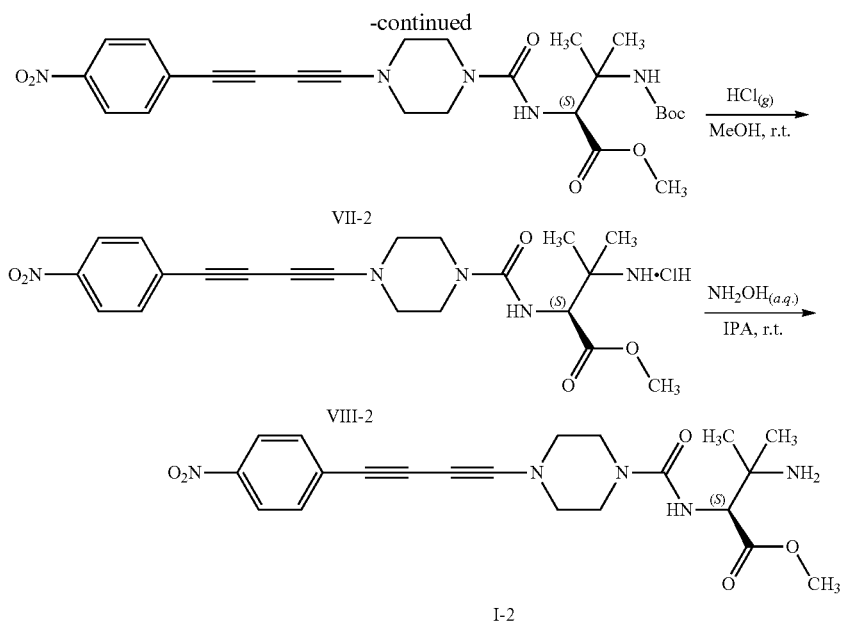

Preparation of 4-nitrobenzaldehyde (III-2)

Dess-Martin periodinane (34.10 g, 80 mmol) was added in portions to a solution of the compound II-2 (11.50 g, 75 mmol) in dichloromethane (250 ml) at −10° C. The addition rate of Dess-Martin periodinane was controlled such that the temperature of the mixture was maintained at −7 to −10° C. On completion of addition, the mixture was stirred at room temperature for 4 h. After the reaction, the reaction mixture was transferred to an ice bath and quenched by addition of saturated aqueous sodium thiosulfate (120 mL) and saturated aqueous sodium hydrogen carbonate (250 mL). The quenched reaction mixture was filtrated to remove solids. The filtrate was allowed to stand for layer separation, and the aqueous layer obtained was extracted 3 times using dichloromethane (120 mL*3). The organic phases obtained were combined and dried over anhydrous sodium sulfate, followed by filtration, concentration under reduced pressure, and purification using silica gel column chromatography (eluent: petroleum ether/ethyl acetate=30:1) to obtain the compound III-2 (7.4 g, 65.2%). MS-APCI (m/z): 152.0[M+H]$^+$

Preparation of 1-(2,2-dibromoethenyl)-4-nitrobenzene (IV-2)

A solution of triphenylphosphine (43.0 g, 165 mmol) in DCM (80 ml) was added dropwise to a solution of carbon tetrabromide (27.2 g, 83 mmol) in DCM (70 ml) at −20° C. under argon atmosphere. On completion of addition, the mixed solution was allowed to react while stirred for 30 min. The resulting reaction mixture was cooled to −78° C., and then a solution of the compound III-2 (6.20 g, 41 mmol) in DCM (60 ml) was added thereto. On completion of addition, the mixture was allowed to react while stirred for 30 min. Thereafter, the reaction mixture after the reaction was allowed to warm to room temperature. The solvent was then distilled off under reduced pressure, and the residue was dissolved in 40% ethanol solution to give a yellow liquid. To the liquid, n-hexane was added, and the mixture was stirred vigorously for 10 min and then was allowed to stand for layer separation. The n-hexane layer obtained was concentrated under reduced pressure to obtain the crude compound IV-2 (10.9 g, 86.9%), which was directly used in the next reaction without purification. A small amount of the crude compound IV-2 was purified using silica gel column chromatography (eluent: petroleum ether/ethyl acetate=150:1) to give a yellow oil. The structure of the oil was then confirmed. MS-ESI (m/z): 327.9[M+Na]$^+$

Preparation of 4-((4-nitrophenyl)butan-1,3-diyne-1-yl)piperazin-1-carboxylic Acid Methyl Ester (V-2)

To DMF (120 ml), the compound IV-2 (7.0 g, 23 mmol), 4-ethynylpiperazin-1-carboxylic acid methyl ester (a-2) (7.7 g, 46 mmol), Pd$_2$(dba)$_3$ (0.6 g, 0.7 mmol), (4-MeOPh)$_3$P (0.5 g, 1.4 mmol), and triethylamine (7.0 g, 70 mmol) were added under argon atmosphere. The mixture was allowed to react at 80° C. for 8 h. After the reaction, ethyl acetate (320 L) was added thereto, and the organic phase was washed using water (200 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=80:1) to obtain the compound V-2 (3.1 g, 42.7%). MS-ESI (m/z): 314.1[M+H]$^+$

Preparation of 4-((4-nitrophenyl)butan-1,3-diyne-1-yl)piperazin-1-carboxylic Acid (VI-2)

To a solution of the compound V-2 (2.2 g, 7 mmol) in THF (80 ml), a solution of NaOH (2.40 g, 70 mmol) in water (10 ml) was added. The mixed solution was allowed to react at room temperature while stirred for 8 h. After the reaction, the solvent was distilled off under reduced pressure. To the residue water (60 ml) was added, and then a 1 mol/L aqueous solution of hydrochloric acid was added thereto to adjust its pH to a value of around 2.0. The resulting mixture was extracted using ethyl acetate (60 ml*4). The organic phases obtained were combined and dried over anhydrous sodium sulfate, followed by filtration and concentration under reduced pressure to give the crude compound VI-2 (1.8 g, 85.8%), which was directly used in the next reaction without purification. A small amount of the crude compound VI-2 was purified to confirm its structure. MS-ESI (m/z): 298.1[M−H]⁻

Preparation of (S)-3-((tert-butoxycarbonyl)amino)-3-methyl-2-(4-((4-nitrophenyl)butan-1,3-diyne-1-yl)piperazin-1-formamido)butyric Acid Methyl Ester (VII-2)

To a solution of the compound VI-2 (6.6 g, 22 mmol) and HATU (10.1 g, 26 mmol) in DMF (180 ml), (S)-methyl 2-amino-3-((tert-butoxycarbonyl)amino)-3-methylbutanoate (Boc-S) (6.4 g, 26 mmol) and DIPEA (11.2 g, 86 mmol) were added. The mixture was allowed to react at room temperature while stirred for 5 h. After the reaction, ethyl acetate (350 ml) was added thereto. The resulting mixture was washed using an aqueous 1.2 mol/L lithium chloride solution (120 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=2:1) to obtain the compound VII-2 (8.0 g, 69.4%). MS-ESI (m/z): 528.3[M+H]⁺)

Preparation of (S)-3-amino-3-methyl-2-(4-((4-nitrophenyl)butan-1,3-diyne-1-yl)piperazin-1-formamido)butyric Acid Methyl Ester (VIII-2)

The compound VII-2 (7.9 g, 15 mmol) was dissolved in methanol (40 ml), and dry hydrogen chloride gas was then introduced into the solution for 30 min. After reaction, the solvent was distilled off under reduced pressure to give the compound VIII-2 (6.0 g, 92.3%), which was directly used in the next reaction without purification. MS-ESI (m/z):428.2 [M+H]⁺

Preparation of (S)—N-(3-amino-1-(hydroxyamino)-3-methyl-1-oxobutan-2-yl)-4-((4-nitrophenyl)butan-1,3-diyne-1-yl)-piperazin-1-formamide (I-2)

The compound VIII-2 (5.6 g, 12 mmol) was dissolved in a mixture of isopropanol (15 ml) and a 16.85 mol/L aqueous hydroxylamine solution (13.8 ml, 230 mmol). The resulting solution was allowed to react at room temperature while stirred until LCMS indicated that the reaction was complete. The reaction mixture was purified using reverse HPLC (chromatography column: XDB-C18 (21.2×250 mm, 7 m); mobile phase A: acetonitrile (containing 0.1% TFA), mobile phase B: water (containing 0.1% TFA); gradient elution: 5 to 30% A from 0 to 40 minutes; column temperature: 25° C.; flow rate: 10 ml/min; detection wavelength: 280 nm), followed by freeze drying, to give the crude compound I-2 (2.19 g, 53.2%). MS-ESI (m/z) 429.2[M+H]⁺. ¹H NMR (500 MHz, CDCl₃) δ9.23 (d, J=4.0 Hz, 1H), 8.72 (d, J=4.2 Hz, 1H), 8.20-8.13 (m, 2H), 7.68 (d, J=10.4 Hz, 1H), 7.75-7.72 (m, 2H), 4.18 (d, J=10.6 Hz, 1H), 3.50-3.42 (m, 4H), 3.15-3.06 (m, 4H), 2.47 (s, 1H), 1.24 (s, 2H), and 1.18 (s, 2H).

Example 3

(S)—N-(3-amino-1-(hydroxyamino)-3-methyl-1-oxobutan-2-yl)-2-hydroxy-4-((4-(piperidin-1-ylmethyl)phenyl)butan-1,3-diyne-1-yl)benzamide (I-3) was prepared according to the following Scheme 6.

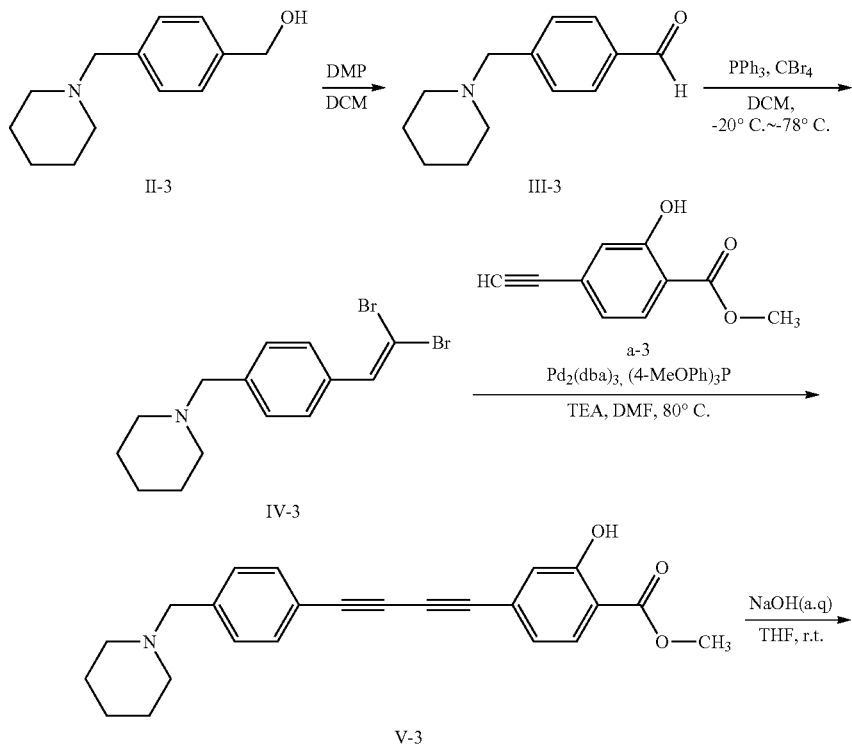

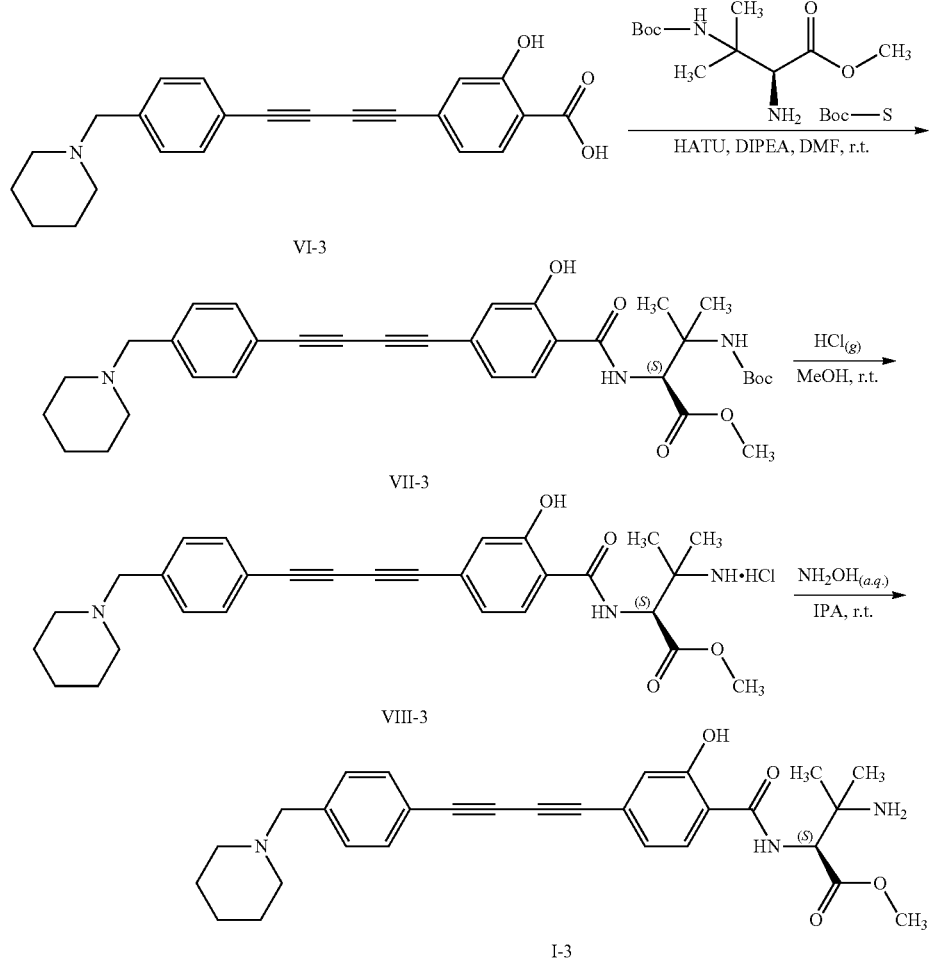

Preparation of 4-(piperidin-1-ylmethyl)benzaldehyde (III-3)

Dess-Martin periodinane (44.5 g, 105 mmol) was added in portions to a solution of the compound II-3 (19.5 g, 95 mmol) in dichloromethane (300 ml) at −10° C. The addition rate was controlled such that the temperature of the reaction mixture was maintained at −7 to −10° C. On completion of addition, the reaction mixture was stirred at room temperature for 4 h. After the reaction, the reaction mixture was transferred to an ice bath and quenched by addition of saturated aqueous sodium thiosulfate (100 mL) and saturated aqueous sodium hydrogen carbonate (250 mL). The quenched reaction mixture was filtrated to remove solids. The filtrate was allowed to stand for layer separation, and the aqueous layer obtained was extracted 3 times using dichloromethane (150 mL*3). The organic phases obtained were combined and dried over anhydrous sodium sulfate, followed by filtration, concentration under reduced pressure, and purification using silica gel column chromatography (eluent: petroleum ether/ethyl acetate=20:1) to obtain the compound III-3 (13.6 g, 70.6%). MS-APCI (m/z): 204.1 [M+H]$^+$

Preparation of 1-(4-(2,2-dibromovinyl)benzyl)piperidine (IV-3)

A solution of triphenylphosphine (45.1 g, 172 mmol) in DCM (90 ml) was added dropwise to a solution of carbon tetrabromide (28.5 g, 86 mmol) in DCM (80 ml) at −20° C. under argon atmosphere. On completion of addition, the mixed solution was allowed to react while stirred for 30 min. The resulting reaction mixture was cooled to −78° C., and then a solution of the compound III-3 (8.7 g, 43 mmol) in DCM (60 ml) was added thereto. On completion of addition, the mixture was allowed to react while stirred for 30 min. Thereafter, the reaction mixture after the reaction was allowed to warm to room temperature. The solvent was then distilled off under reduced pressure, and the residue was dissolved in 40% ethanol solution to give a yellow liquid. To the liquid, n-hexane was added, and the mixture was stirred vigorously for 10 min and then was allowed to stand for layer separation. The n-hexane layer obtained was concentrated under reduced pressure to obtain the crude compound IV-3 (13.0 g, 84.7%), which was directly used in the next reaction without purification. A small amount of the crude compound IV-3 was purified using silica gel column chromatography (eluent: petroleum ether/ethyl acetate=150:1) to give a yellow oil. The structure of the oil was then confirmed. MS-ESI (m/z): 380.1[M+Na]$^+$

Preparation of 2-hydroxy-4-((4-(piperidin-1-ylmethyl)phenyl)butan-1,3-diyne-1-yl)benzoic Acid Methyl Ester (V-3)

To DMF (120 ml), the compound IV-3 (10.7 g, 30 mmol), methyl 4-ethynyl-2-hydroxybenzoate (a-3) (10.6 g, 60 mmol), Pd$_2$(dba)$_3$ (0.81 g, 0.9 mmol), (4-MeOPh)$_3$P (0.62 g, 1.8 mmol), and triethylamine (8.92 g, 88 mmol) were added under argon atmosphere. The mixture was allowed to react at 80° C. for 8 h. After the reaction, ethyl acetate (300 L) was added thereto, and the mixture was washed using water (150 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=80:1) to obtain the compound V-3 (4.23 g, 37.8%). MS-ESI (m/z): 374.2[M+H]$^+$ Preparation of 2-hydroxy-4-((4-(piperidin-1-ylmethyl)phenyl)butan-1,3-diyne-1-yl)benzoic Acid (VI-3)

To a solution of the compound V-3 (3.4 g, 9 mmol) in THF (60 ml), a solution of NaOH (3.6 g, 90 mmol) in water (20 ml) was added. The mixed solution was allowed to react at room temperature while stirred for 8 h. After the reaction, the solvent was distilled off under reduced pressure. To the residue water (50 ml) was added, and then a 1 mol/L aqueous solution of hydrochloric acid was added thereto to adjust its pH to a value of around 2.0. The resulting mixture was extracted using ethyl acetate (50 ml*4). The organic phases obtained were combined and dried over anhydrous sodium sulfate, followed by filtration and concentration under reduced pressure to give the crude compound VI-3 (2.8 g, 86.6%), which was directly used in the next reaction without purification. A small amount of the crude compound VI-3 was purified to confirm its structure. MS-ESI (m/z): 358.2[M–H]$^-$ Preparation of (S)-3-((tert-butoxycarbonyl)amino)-2-(2-hydroxy-4-((4-(piperidin-1-ylmethyl)phenyl)butan-1,3-diyne-1-yl)benzoylamino)-3-methyl-butyric Acid Methyl Ester (VII-3)

To a solution of the compound VI-3 (9.7 g, 27 mmol) and HATU (12.90 g, 33 mmol) in DMF (170 ml), (S)-methyl 2-amino-3-((tert-butoxycarbonyl)amino)-3-methylbutanoate (Boc-S) (8.15 g, 33 mmol) and DIPEA (14.25 g, 110 mmol) were added. The mixture was allowed to react at room temperature while stirred for 5 h. After the reaction, ethyl acetate (320 ml) was added thereto. The resulting mixture was washed using an aqueous 1.2 mol/L lithium chloride solution (120 ml*3). The organic phase obtained was dried over anhydrous sodium sulfate, followed by filtration and concentration under reduced pressure to give a crude product. The crude product was purified using silica gel column chromatography (eluent: petroleum ether/ethyl acetate=2:1) to obtain the compound VII-3 (11.2 g, 70.8%). MS-ESI (m/z): 588.3[M+H]$^+$)

Preparation of (S)-3-amino-2-(2-hydroxy-4-((4-(piperidin-1-ylmethyl)phenyl)butan-1,3-diyne-1-yl)benzoylamino)-3-methyl-butyric Acid Methyl Ester (VIII-2)

The compound VII-2 (11.2 g, 19 mmol) was dissolved in methanol (40 ml), and dry hydrogen chloride gas was then introduced into the solution for 35 min. After reaction, the solvent was distilled off under reduced pressure to give the compound VIII-3 (8.6 g, 92.6%), which was directly used in the next reaction without purification. MS-ESI (m/z):488.5 [M+H]$^+$ Preparation of (S)—N-(3-amino-1-(hydroxyamino)-3-methyl-1-oxobutan-2-yl)-2-hydroxy-4-((4-(piperidin-1-ylmethyl)phenyl)butan-1,3-diyne-1-yl)benzamide (I-3)

The compound VIII-3 (7.3 g, 15 mmol) was dissolved in a mixture of isopropanol (15 ml) and a 16.85 mol/L aqueous hydroxylamine solution (17.5 ml, 295 mmol). The resulting solution was allowed to react at room temperature while stirred until LCMS indicated that the reaction was complete. The reaction mixture after the reaction was purified using reverse HPLC (chromatography column: XDB-C18 (21.2× 250 mm, 7 μm); mobile phase A: acetonitrile (containing 0.1% TFA), mobile phase B: water (containing 0.1% TFA); gradient elution: 5 to 30% A from 0 to 40 minutes; column temperature: 25° C.; flow rate: 10 ml/min; detection wavelength: 280 nm), followed by freeze drying, to give the compound I-3 (3.7 g, 50.8%). MS-ESI (m/z) 489.2[M+H]$^+$. $^1$H NMR (500 MHz, CDCl$_3$) δ9.18 (d, J=4.0 Hz, 1H), 8.74 (d, J=4.0 Hz, 1H), 8.53 (d, J=10.8 Hz, 1H), 7.82-7.75 (m, 1H), 7.50-7.43 (m, 2H), 7.30-7.26 (m, 2H), 7.20-7.15 (m, 2H), 4.28 (d, J=10.8 Hz, 2H), 3.55-3.48 (m, 2H), 2.47-2.38 (m, 6H), 1.60-1.46 (m, 4H), 1.46-1.34 (m, 2H), 1.18 (s, 2H), and 1.11 (s, 2H).

Test Example

An antibiotic susceptibility test was carried out using the broth microdilution guidelines as stipulated by the Clinical and Laboratory Standards Institute (CLSI). Test organisms were grown in Mueller-Hinton (MH) or Brain Heart Infusion (BHI) broth. Solutions of compounds to be tested were each diluted in 96-well plates (50 μl per well) to various prescribed concentrations with the MH or BHI broth. Final concentrations of the solutions in each well were as follows: 128, 64, 32, 16, 8, 4, 2, 1, 0.5, 0.25, 0.125, 0.06, and 0.03 μg/ml. The culture mediums in the 96-well plates were inoculated with 5×10$^5$ CFU/ml of the test organisms, and then the organisms were cultured at 35° C. for 18 h. The results are shown in Table 1.

TABLE 1

| | Minimal inhibitory concentrations (MICs/μg · ml$^{-1}$) of levofloxacin, and compounds I-1, I-2, and I-3 | | | | | |
|---|---|---|---|---|---|---|
| Compound | E. coli ATCC 25922 | Klebsiella pneumoniae ATCC 700603 | NDM-1-producing Klebsiella pneumoniae ATCC 2146 | Enterobacter cloacae ATCC 43560 | Enterobacter aerogenes ATCC 13048 | Pseudomonas aeruginosa ATCC 27853 |
| I-1 | 0.125 | 2 | 2 | 1 | 1 | 0.5 |
| I-2 | 0.125 | 2 | 2 | 0.5 | 2 | 0.25 |

TABLE 1-continued

Minimal inhibitory concentrations (MICs/μg · ml⁻¹) of levofloxacin, and compounds I-1, I-2, and I-3

| Compound | E. coli ATCC 25922 | Klebsiella pneumoniae ATCC 700603 | NDM-1-producing Klebsiella pneumoniae 2146 | Enterobacter cloacae ATCC 43560 | Enterobacter aerogenes ATCC 13048 | Pseudomonas aeruginosa ATCC 27853 |
|---|---|---|---|---|---|---|
| I-3 | 0.125 | 4 | 2 | 1 | 2 | 0.5 |
| Levofloxacin | ≤0.25 | 0.5 | >64 | ≤0.25 | ≤0.25 | 1 |

It can be seen from Table 1 that the compounds I-1, I-2, and I-3 have bactericidal activity against a variety of gram negative bacteria, and are especially superior to levofloxacin (which is used as a first-line medicine in clinical practice) in their bactericidal activity against NDM-1-producing *Klebsiella pneumoniae* 2146 and *Pseudomonas aeruginosa* ATCC27853.

ICR mice of either sex weighing between 18-22 g were randomized into groups of 3 mice per group. The mice were given the compound D73-ACHN975, I-1, I-2, or I-3 via tail vein injection at doses shown in Table 2, and were monitored after injection. The number of mice that died and the time of death were recorded. Based on these data, the mortality rate was then calculated. Tails were removed from the mice that were not dead from the injection and from the normal mice that were not given any of the compounds, and were then fixed in paraformaldehyde. Tail vessels were observed by HE staining to determine whether or not a lesion existed. The results are shown in Table 2.

TABLE 2

Results of experiments of toxicity in mice obtained with compounds D73-ACHN975, I-1, I-2, and I-3

| Compound | Dose/ (mg/kg) | Number of mice tested | Number of deaths | Mortality rate/% | Time of death/ min | Toxicity/ yes or no |
|---|---|---|---|---|---|---|
| D73-ACHN975 | 75 | 3 | 0 | 0 | — | yes |
|  | 100 | 3 | 1 | 33 | 0.5-2 | yes |
|  | 150 | 3 | 3 | 100 | 0.5-1 | yes |
| I-1 | 100 | 3 | 0 | 0 | — | no |
|  | 200 | 3 | 2 | 66 | 10-20 | yes |
|  | 300 | 1 | 1 | 100 | 1 | yes |
| I-2 | 100 | 3 | 0 | 0 | — | no |
|  | 200 | 3 | 2 | 66 | 10-15 | yes |
|  | 300 | 1 | 1 | 100 | 0.5-1 | yes |
| I-3 | 100 | 3 | 0 | 0 | — | no |
|  | 200 | 3 | 2 | 66 | 10-20 | yes |
|  | 300 | 1 | 1 | 100 | 1 | yes |

It can be seen from Table 2 that the maximum tolerated dose (MTD) of the compound D73-ACHN975 is around 75 mg/kg, while the MTD of each of the compounds I-1, I-2, and I-3 is greater than 100 mg/kg. It was estimated that the $LD_{50}$ value of the compound D73-ACHN975 for ICR mice is less than that of the compounds I-1, I-2, and I-3 when intravenously administered. However, the specific values need to be further determined. So, it can be determined that the acute intravenous toxicity in mice of the compounds I-1, I-2, and I-3 is below that of the compound D73-ACHN975.

From the results described above, it can be seen that the hydroxamic acid derivative of the disclosure exhibits good bactericidal activity and low toxicity.

The embodiments described above are only intended to help in understanding the methodology and idea of the present disclosure. It will be understood by those skilled in the art that various improvements and modifications may be made without departing from the principle of the present disclosure, and shall fall within the scope of the disclosure as defined by the appended claims. Various modifications to these embodiments will be readily apparent to those skilled in the art, and the generic principles described herein can be applied to other embodiments without departing from the spirit or scope of the present disclosure. Thus, the disclosure is not intended to be limited to the embodiments described herein but is to be accorded the widest scope consistent with the principles and novel features disclosed herein.

What is claimed is:

1. A hydroxamic acid derivative, having a structure of following Formula (I):

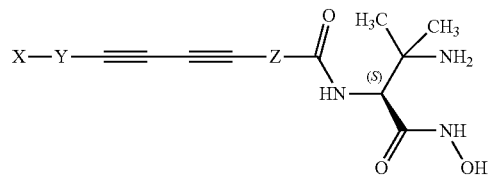

Formula (I)

wherein,

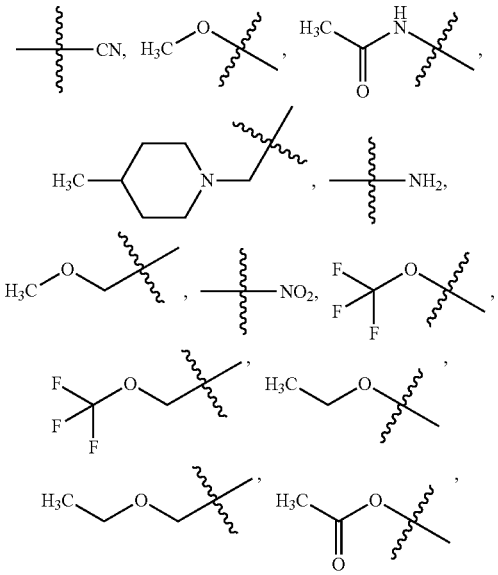

-continued
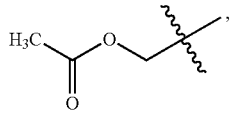
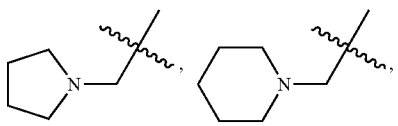
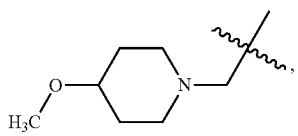
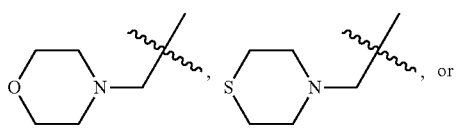
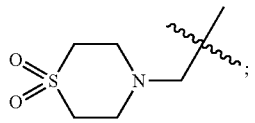
Y is
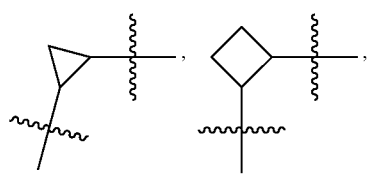
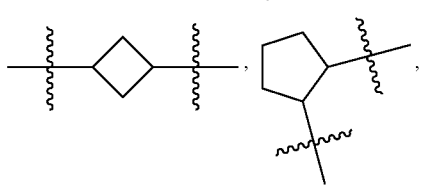
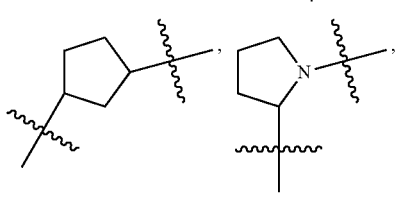
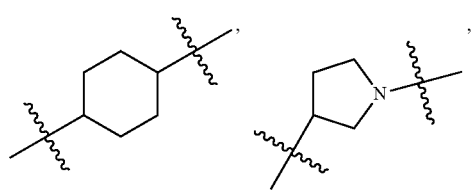
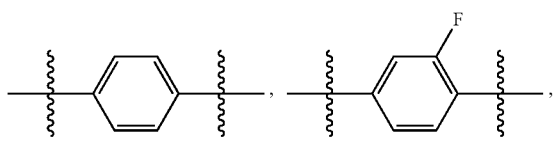
-continued
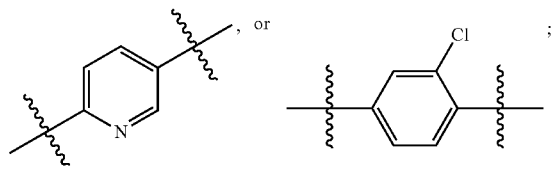
and
Z is
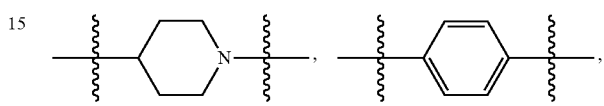
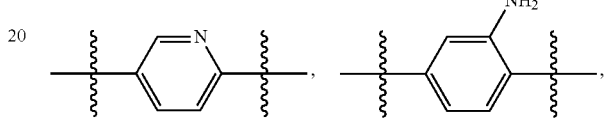
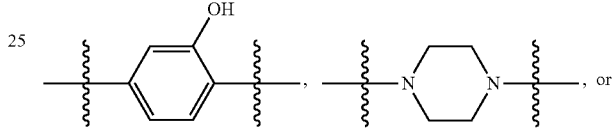
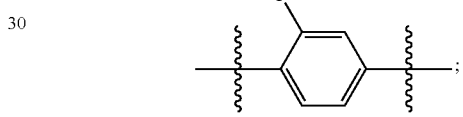
wherein, when Y and Z are
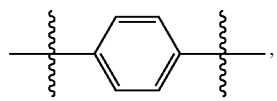
X is not
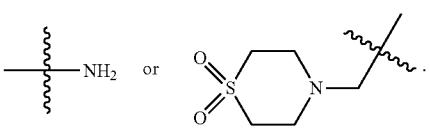
2. A hydroxamic acid derivative having a Formula (I):
wherein,
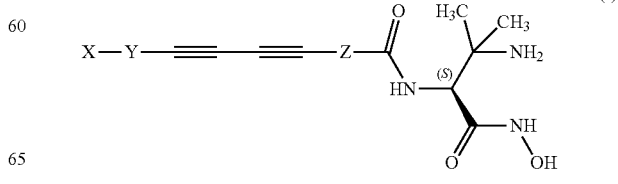

wherein
X is

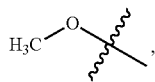 , 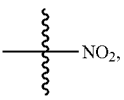 or

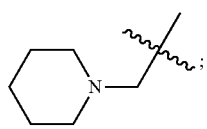

Y is

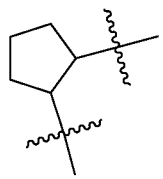 or 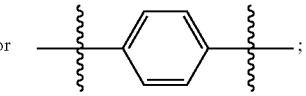 ;

and
Z is

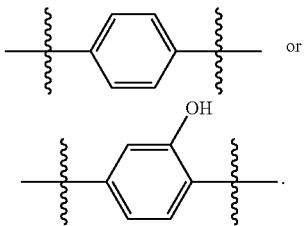.

3. A method for producing the hydroxamic acid derivative according to claim 1, comprising steps of:

mixing a compound having a structure of following Formula (II) with Dess-Martin periodinane and dichloromethane to conduct an oxidation reaction, so as to obtain a compound having a structure of following Formula (III);

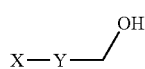
Formula (II)

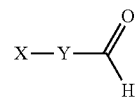
Formula (III)

mixing the compound of Formula (III) with triphenylphosphine, carbon tetrabromide (CBr$_4$), and dichloromethane to conduct the Corey-Fuchs reaction, so as to obtain a compound having a structure of following (IV);

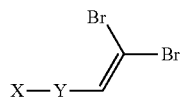
Formula (IV)

mixing the compound of Formula (IV) with tris(dibenzylideneacetone)dipalladium (Pd$_2$(dba)$_3$), a compound having a structure of following Formula (a), triethylamine, and N,N-dimethylformamide to conduct a Sonogashira coupling reaction, so as to obtain a compound having a structure of following Formula (V);

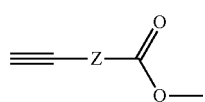
Formula (a)

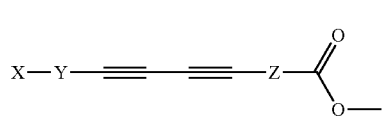
Formula (V)

mixing the compound of Formula (V) with tetrahydrofuran and a sodium hydroxide solution to conduct a hydrolysis reaction, so as to obtain a compound having a structure of following Formula (VI);

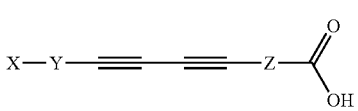
Formula (VI)

mixing the compound of Formula (VI) with (S)-methyl 2-amino-3-((tert-butoxycarbonyl)amino)-3-methylbutanoate, diisopropylethylamine, O-(7-azabenzotriazol-1-yl)-N,N,N',N'-tetramethyluronium hexafluorophosphate, and N,N-dimethylformamide to conduct a condensation reaction, so as to obtain a compound having a structure of following Formula (VII);

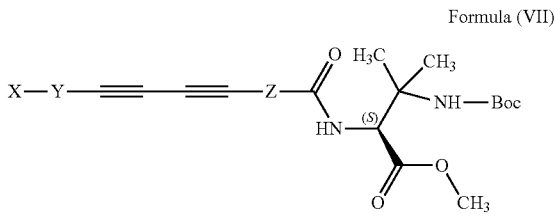
Formula (VII)

mixing the compound of Formula (VII) with methanol and hydrogen chloride gas to conduct a Boc-deprotection reaction, so as to obtain a compound having a structure of following Formula (VIII); and

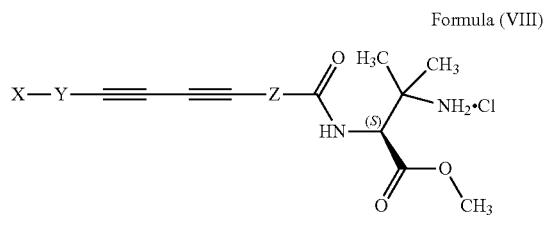

Formula (VIII)

mixing the compound of Formula (VIII) with isopropanol and an aqueous solution of hydroxylamine to conduct a substitution reaction, so as to obtain the compound of Formula (I).

4. A method for producing the hydroxamic acid derivative according to claim 2, comprising steps of:

mixing a compound having a structure of following Formula (II) with Dess-Martin periodinane and dichloromethane to conduct an oxidation reaction, so as to obtain a compound having a structure of following Formula (III);

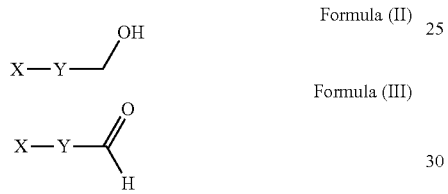

Formula (II)

Formula (III)

mixing the compound of Formula (III) with triphenylphosphine, carbon tetrabromide (CBr$_4$), and dichloromethane to conduct the Corey-Fuchs reaction, so as to obtain a compound having a structure of following (IV);

Formula (IV)

mixing the compound of Formula (IV) with tris(dibenzylideneacetone)dipalladium (Pd$_2$(dba)$_3$), a compound having a structure of following Formula (a), triethylamine, and N,N-dimethylformamide to conduct a Sonogashira coupling reaction, so as to obtain a compound having a structure of following Formula (V);

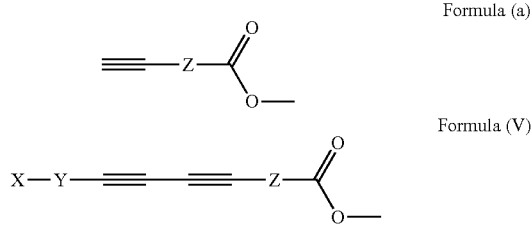

Formula (a)

Formula (V)

mixing the compound of Formula (V) with tetrahydrofuran and a sodium hydroxide solution to conduct a hydrolysis reaction, so as to obtain a compound having a structure of following Formula (VI);

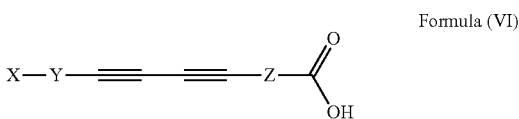

Formula (VI)

mixing the compound of Formula (VI) with (S)-methyl 2-amino-3-((tert-butoxycarbonyl)amino)-3-methylbutanoate, diisopropylethylamine, O-(7-azabenzotriazol-1-yl)-N,N,N',N'-tetramethyluronium hexafluorophosphate, and N,N-dimethylformamide to conduct a condensation reaction, so as to obtain a compound having a structure of following Formula (VII);

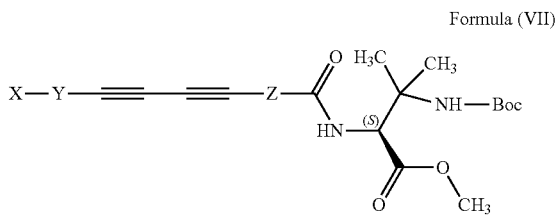

Formula (VII)

mixing the compound of Formula (VII) with methanol and hydrogen chloride gas to conduct a Boc-deprotection reaction, so as to obtain a compound having a structure of following Formula (VIII); and

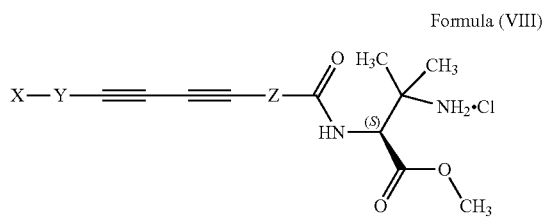

Formula (VIII)

mixing the compound of Formula (VIII) with isopropanol and an aqueous solution of hydroxylamine to conduct a substitution reaction, so as to obtain the compound of Formula (I).

5. The method according to claim 3, wherein, the molar ratio of the Dess-Martin periodinane to the compound of Formula (II) is 1.0 to 1.2.

6. The method according to claim 4, wherein, the molar ratio of the Dess-Martin periodinane to the compound of Formula (II) is 1.0 to 1.2.

7. The method according to claim 3, wherein, the oxidation reaction is conducted at room temperature for 2 to 8 hours.

8. The method according to claim 5, wherein, the oxidation reaction is conducted at room temperature for 2 to 8 hours.

9. The method according to claim 3, wherein, the molar ratio of the compound of Formula (III)/triphenylphosphine/carbon tetrabromide is 1:(3.8-4.2):(1.8-2.2).

10. The method according to claim 3, wherein, the Corey-Fuchs reaction is conducted at a temperature of −20 to −78° C.

11. The method according to claim 9, wherein, the Corey-Fuchs reaction is conducted at a temperature of −20 to −78° C.

12. The method according to claim 3, wherein, the molar ratio of the compound of Formula (IV)/tris(dibenzylideneacetone)dipalladium/the compound of Formula (a)/triethylamine is 1:(0.02-0.04):(1.8-2.2):(2.8-3.2).

13. The method according to claim 3, wherein, the Sonogashira coupling reaction is conducted at a temperature of 75 to 85° C. for 6 to 10 hours.

14. The method according to claim 12, wherein, the Sonogashira coupling reaction is conducted at a temperature of 75 to 85° C. for 6 to 10 hours.

15. The method according to claim 3, wherein, the molar ratio of sodium hydroxide in the sodium hydroxide solution to the compound of Formula (V) is 8 to 12.

16. The method according to claim 3, wherein, the hydrolysis reaction is conducted at room temperature for 6 to 10 hours.

17. The method according to claim 3, wherein, the molar ratio of the compound of Formula (VI)/(S)-methyl 2-amino-3-((tert-butoxycarbonyl)amino)-3-methylbutanoate/diisopropylethyl amine/O-(7-azabenzotriazol-1-yl)-N,N,N',N'-tetramethyluronium hexafluorophosphate is 1:(1.1~1.3):(3.8~4.2):(1.1~1.3).

18. The method according to claim 3, wherein, the condensation reaction is conducted at room temperature for 3 to 8 hours.

19. The method according to claim 3, wherein, the molar ratio of hydroxylamine in the aqueous solution of hydroxylamine to the compound of Formula (VIII) is 18 to 22.

* * * * *